United States Patent
Remis et al.

(10) Patent No.: US 8,020,724 B2
(45) Date of Patent: Sep. 20, 2011

(54) VACUUM BASED PILL SINGULATOR AND COUNTER BASED THEREON

(75) Inventors: Steven J. Remis, Alexandria, LA (US);
Adam Hahn, Pittsburgh, PA (US);
Raymond Rhodes, Pittsburgh, PA (US);
John Volkar, Mars, PA (US)

(73) Assignee: Parata Systems, LLC, Durham, NC (US)

( * ) Notice: Subject to any disclaimer, the term of this patent is extended or adjusted under 35 U.S.C. 154(b) by 816 days.

(21) Appl. No.: 10/972,556

(22) Filed: Oct. 25, 2004

(65) Prior Publication Data
US 2005/0224510 A1    Oct. 13, 2005

Related U.S. Application Data

(60) Provisional application No. 60/553,193, filed on Mar. 15, 2004.

(51) Int. Cl.
*B65G 59/04* (2006.01)
*B65H 3/08* (2006.01)
*G07F 11/00* (2006.01)

(52) U.S. Cl. .......... 221/211; 221/4; 221/7; 221/13; 221/197; 221/168; 221/69; 111/179; 111/77; 111/185; 198/47.1; 198/397; 198/453

(58) Field of Classification Search .......... 198/471.1, 198/397, 453; 452/31; 221/4, 7, 13, 211, 221/197, 168, 69; 111/179, 77, 185
See application file for complete search history.

(56) References Cited

U.S. PATENT DOCUMENTS

| | | | | |
|---|---|---|---|---|
| 3,533,535 A | * | 10/1970 | Knapp | 221/211 |
| 3,533,801 A | | 10/1970 | Wenger | |
| 3,770,164 A | | 11/1973 | Hembree | |
| 4,697,721 A | * | 10/1987 | Johnson et al. | 221/211 |

(Continued)

FOREIGN PATENT DOCUMENTS
WO    WO 03/008308 A1    1/2003

*Primary Examiner* — Gene O. Crawford
*Assistant Examiner* — Rakesh Kumar
(74) *Attorney, Agent, or Firm* — Myers Bigel Sibley & Sajovec

(57) ABSTRACT

A singulating disc, carried by a housing, has a plurality of openings around its periphery. The disc rotates vertically through a pickup chamber of a hopper carried by the housing. A vacuum is pulled through the openings by a pump which is connected to the disc. Items are placed in the hopper and, via gravity, fall to the bottom of the hopper where they contact the periphery of the rotating disc. The vacuum at the openings attaches an item and holds it while the disc rotates. At the top of the disc's rotation, a diverter directs the item into a path depending on the results of a fragment detection and/or counting mechanism. Items that are allowed to pass by the diverter are scraped off the disc into another path by a scraper. Negative pressure is used to singulate and count a multitude of sizes and shapes of items with no calibration. Retractable paddles, a vacuum management system, and RFID tags may be incorporated. The paddles aid in the pickup and agitation of the items while the vacuum management system conserves the vacuum capacity necessary to pickup and singulate items. The RFID tags may contain information such as the number of items left in the hopper, a par level for that item, an expiration date, among others. Because of the rules governing abstracts, this abstract should not be used to construe the claims.

13 Claims, 25 Drawing Sheets

U.S. PATENT DOCUMENTS

| | | | |
|---|---|---|---|
| 4,741,428 A * | 5/1988 | Taniguchi et al. | 198/397.04 |
| 5,325,801 A * | 7/1994 | Fiorido | 111/185 |
| 6,036,812 A | 3/2000 | Williams et al. | |
| 6,053,302 A * | 4/2000 | Leu et al. | 198/471.1 |
| 6,135,120 A * | 10/2000 | Lofman et al. | 131/112 |
| 6,276,564 B1 * | 8/2001 | Reich | 221/217 |
| 6,370,215 B1 | 4/2002 | Pinto et al. | |
| 6,484,902 B1 | 11/2002 | Rouse | |
| 6,561,377 B1 | 5/2003 | Pearson et al. | |
| 6,799,413 B2 | 10/2004 | Aylward | |
| 6,997,341 B2 * | 2/2006 | Pearson et al. | 221/7 |
| 7,004,353 B2 | 2/2006 | Yamamoto et al. | |
| 7,014,063 B2 * | 3/2006 | Shows et al. | 221/211 |
| 7,099,741 B2 | 8/2006 | Baranowski | |
| 2003/0006281 A1 * | 1/2003 | Thomas et al. | 235/385 |
| 2003/0015555 A1 | 1/2003 | Pollard et al. | |
| 2003/0116068 A1 | 6/2003 | Sauder et al. | |
| 2004/0104241 A1 * | 6/2004 | Broussard et al. | 221/289 |

\* cited by examiner

VACUUM BASED PILL SINGULATOR AND COUNTER BASED THEREON

This application claims priority from U.S. Patent Application Ser. No. 60/553,193 filed Mar. 15, 2004 and entitled Vacuum Based Pill Singulator and Counter Base Thereon, the entirety of which is hereby incorporated by reference.

BACKGROUND

The present disclosure is directed to singulators for singulating items such as pills from a bulk supply and, more particularly, to singulators of the type having a conveying wheel rotating through the bulk supply of items to be singulated.

Singulating items from a bulk supply is a difficult task, particularly where the items must be precisely counted, such as is the case with pharmaceuticals. The singulating task is complicated by the fact that the device for singulating often times must be able to singulate items of varying sizes, shapes and weights.

One example of a singulating device and counter is found in U.S. Pat. No. 4,018,358 entitled Cassette Pill Storing, Dispensing and Counting Machine. In that patent, different types of pills are stored in separate cassettes which may be operated by a dispensing machine for dispensing from the cassette into a vial. The dispensing machine provides a vacuum supply and a rotary drive for operating a wheel in the cassette having a series of openings annularly arranged to pick up pills in the bottom of the cassette under vacuum pressure and carry them to a discharge opening. A separator wall extending across the line of travel of the holes carrying pills deflects the pills through the discharge opening. A gauge is adjustable to overlie a portion of the openings in the wheel to vary the opening size so that only a single pill is carried by each opening. A photoelectric cell triggered by a fiber optic scanner at the discharge opening counts each pill. An agitator turns with the conveying wheel to break up pills bridged together. A switch is utilized to set an electronic counter to the number of pills desired. This counter then successively counts down until it reaches zero at which point the machine stops.

Another example of a singulating device and counter is found in U.S. Pat. No. 4,697,721 entitled Pill Storage and Dispensing Cassette which discloses an improved pill storage and dispensing cassette having front and back side walls, opposite end walls, and opposite top and bottom walls defining a storage chamber therein. A rotatable pill conveying wheel is positioned in the back side wall and has a plurality of openings for holding and conveying a pill to a discharge chute upon actuation of a remote vacuum source. A separator member is positioned over the openings of the conveying wheel to dislodge the pills from the conveying wheel and such that the pills fall through the chute into the desired receptacle. An adjustment shoe is provided so that only one pill is held and conveyed by each opening in the conveying wheel. A central wall is included within the cassette to divide the pill chamber into forward and rearward compartments with the pills being primarily stored in the forward compartment with a limited number of pills passing through a recessed area in the central wall to the rearward compartment for conveyance by the conveying wheel. An agitator is positioned within the rearward compartment for rotation in the opposite direction as the conveying wheel to agitate the pills and prevent bridging across the top surface thereof. An insert is provided at the opening of the discharge chute to direct the dislodged pills into a receiving vial. The cassette is used in conjunction with a counter that provides a source of rotary motion for the conveying wheel as well as a vacuum source.

Another example of a singulating device and counter is found in U.S. Pat. No. 6,561,377 entitled Vacuum Drum Pill Counter which discloses a vacuum driven pill counter having a counter housing with a pill discharge aperture formed therein. An integrally formed vacuum drum is rotatably positioned in the housing and the vacuum drum includes a front wall, a rear wall, and a perimeter wall. The front wall of the vacuum drum has a plurality of pill apertures formed therein. A vacuum source communicates with the housing such that the vacuum sources is capable of drawing a vacuum through the pill apertures formed in the vacuum drum and a torque source is operatively connected to the vacuum drum to rotate the vacuum drum. A pill shelf is positioned adjacent to the front wall of the vacuum drum and a pill separator removes pills retained on the pill apertures while a pill sensor detects pills which are removed by the pill separator and exit the discharge aperture.

Other examples of singulating devices that rely upon a rotating drum having openings at which a vacuum is present are found in U.S. Pat. No. 3,770,164 entitled Singulator for Seeds or the Like (see particularly FIG. 7) and U.S. publication no. 2003/0116068 A1 entitled Vacuum Seed Meter and Dispensing Apparatus.

BRIEF SUMMARY

The present disclosure is directed to a singulating device comprising a pickup chamber, a housing and a hollow, rotatable singulating disc (as disclosed herein) or a non-hollow disc (as in U.S. Pat. No. 4,018,358) having a plurality of openings around the periphery thereof. The disc is carried by a housing such that a portion of the disc rotates through the pickup chamber. A source of rotary motion and a vacuum source are coupled to the singulating disc. First, second and third pill (or other item being singulated) paths are provided as is an inspection and/or counting device. Means are responsive to the inspecting and counting device for removing items from the singulating disc in a manner that directs the removed items into one of the first, second or third paths.

The present disclosure is also directed to a singulating device comprising a pickup chamber, a housing and a hollow, rotatable, singulating disc having a plurality of openings around the periphery thereof. The disc is carried by the housing such that a portion of the disc rotates through the pickup chamber. The disc has a plurality of retractable paddles extendable from the periphery, with each of the paddles having an actuating device (e.g. a pin) extending through an opening (e.g. a slot) in a face of the singulating disc. A source of rotary motion and a vacuum source are coupled to the singulating disc. At least one pill (or other item being singulated) path is provided. Means, such as a diverter, scraper, wiper or the like, are provided for removing items from the periphery of the singulating disc into the path. A cam is positioned to interface with each of the actuating pins during a portion of rotation of the singulating disc such that each of the pins moves along the slot in a first direction to cause its respective paddle to extend beyond the periphery, and to move along the slot in a second direction opposite to the first direction to cause the paddle to retract as the pin rides along the cam. An input splitter, responsive to the source of rotary motion, may be provided so that one source of rotary motion can be used to both drive the singulating disc and to control the position of the cam.

The present disclosure is also directed to a singulating device comprising a pickup chamber, a housing and a hollow, rotatable, singulating disc having a plurality of openings around the periphery thereof. The disc is carried by the housing such that a portion of the disc rotates through the pickup chamber. The disc has a plurality of pistons, each piston positioned so as to control or regulate the volume of air flowing through one of the plurality of openings. A source of rotary motion and a vacuum source are coupled to the singulating disc. At least one pill (or other item being singulated) path is provided. Means, such as a diverter, scraper, wiper or the like, are provided for removing items from the periphery of the singulating disc into the path. A cam is positioned to interface with each of the pistons during a portion of rotation of the singulating disc such that each of the pistons is fully retracted from its respective opening while the opening is located in the pickup chamber. The cam causes each piston to be fully extended to block its respective opening while that opening rotates from the means for removing to the pickup chamber.

The present disclosure is also directed to a singulating device comprising a removable hopper having a pickup chamber accessed by a door. The hopper is carried by a housing. Also carried by the housing is a rotatable singulating disc, either hollow or non-hollow, having a plurality of openings around the periphery thereof. A portion of the disc rotates through the pickup chamber when the hopper is attached to the housing. A source of rotary motion and a vacuum source are coupled to the singulating disc. At least one pill (or other item being singulated) path is provided. Means, such as a diverter, scraper, wiper or the like, are provided for removing items from the periphery of the singulating disc into the path. The door on the hopper is configured to wipe any items from the singulating disc into the pickup chamber upon removal of the hopper from the singulating disc.

The present disclosure is also directed to various methods of operating the disclosed apparatus. According to one method, a singulating disc is rotated through a pickup chamber while a vacuum is pulled at a plurality of openings located around a periphery of the disc. Items captured by the singulating discs are inspected and/or counted. The items captured by the singulating discs are removed in a manner such that the items are directed into one of a first, second or third path based on either the inspecting, the counting, or other machine control objectives, or any combination of such objectives.

Another disclosed method of singulating items is comprised of rotating a portion of a hollow, singulating disc through a pickup chamber while pulling a vacuum at a plurality of openings located around the periphery of the disc. As the disc is rotating, paddles are extended from the periphery of that portion of the singulating disc located in the pickup chamber. The extended paddles are then retracted and the items captured by the singulating disc removed. The method may further include ceasing rotation of the disc, retracting all of the paddles, and removing a removable hopper from a housing carrying the singulating disc.

Another method of singulating items comprises rotating a portion of a hollow, singulating disc through a pickup chamber while pulling a vacuum at a plurality of openings located around the periphery of the disc. As the disc is rotating, the volume of air flowing through each of the plurality of openings is controlled. Items captured by the singulating disc are removed. The method additionally comprises maximizing the air flow when an opening is in the pickup chamber and minimizing the air flow for an opening during the removing of an item.

The present disclosure is further directed to a method of singulating items comprising attaching a hopper having a pickup chamber to a housing having a singulating wheel. A portion of the singulating disc is rotated through the pickup chamber while a vacuum is pulled at a plurality of openings located around the periphery of the disc. Items captured by the singulating disc are removed. The rotation of the disc is ceased and the hopper is detached from the housing such that the hopper's access doors wipe any items from the disc into the pickup chamber as the hopper is detached and the access doors are closed.

The present disclosure is directed to a variety of methods and apparatus. Those of ordinary skill in the art will recognize that many components may be used individually, or in combination with other components, with the method accordingly modified. For example, a hollow, singulating disc can be used which has retractable paddles, with or without pistons for controlling the air flow. Similarly, a hollow, singulating wheel may be used having pistons for controlling the air flow, with or without retractable paddles. Thus, the fact that certain components have been grouped together for purposes of description should not be understood to mean that the components can only be used in the disclosed groupings.

BRIEF DESCRIPTION OF THE DRAWINGS

For the present disclosure to be easily understood and readily practiced, the present disclosure will now be described, for purposes of illustration and not limitation, in conjunction with the following figures, wherein:

FIGS. 2A and 2B illustrate another embodiment of a singulating device constructed according to the present disclosure while

FIGS. 15A and 15B illustrate control mechanisms for controlling the number of pills allowed to occupy the pickup chamber within the hopper while

DETAILED DESCRIPTION

Figure 1:
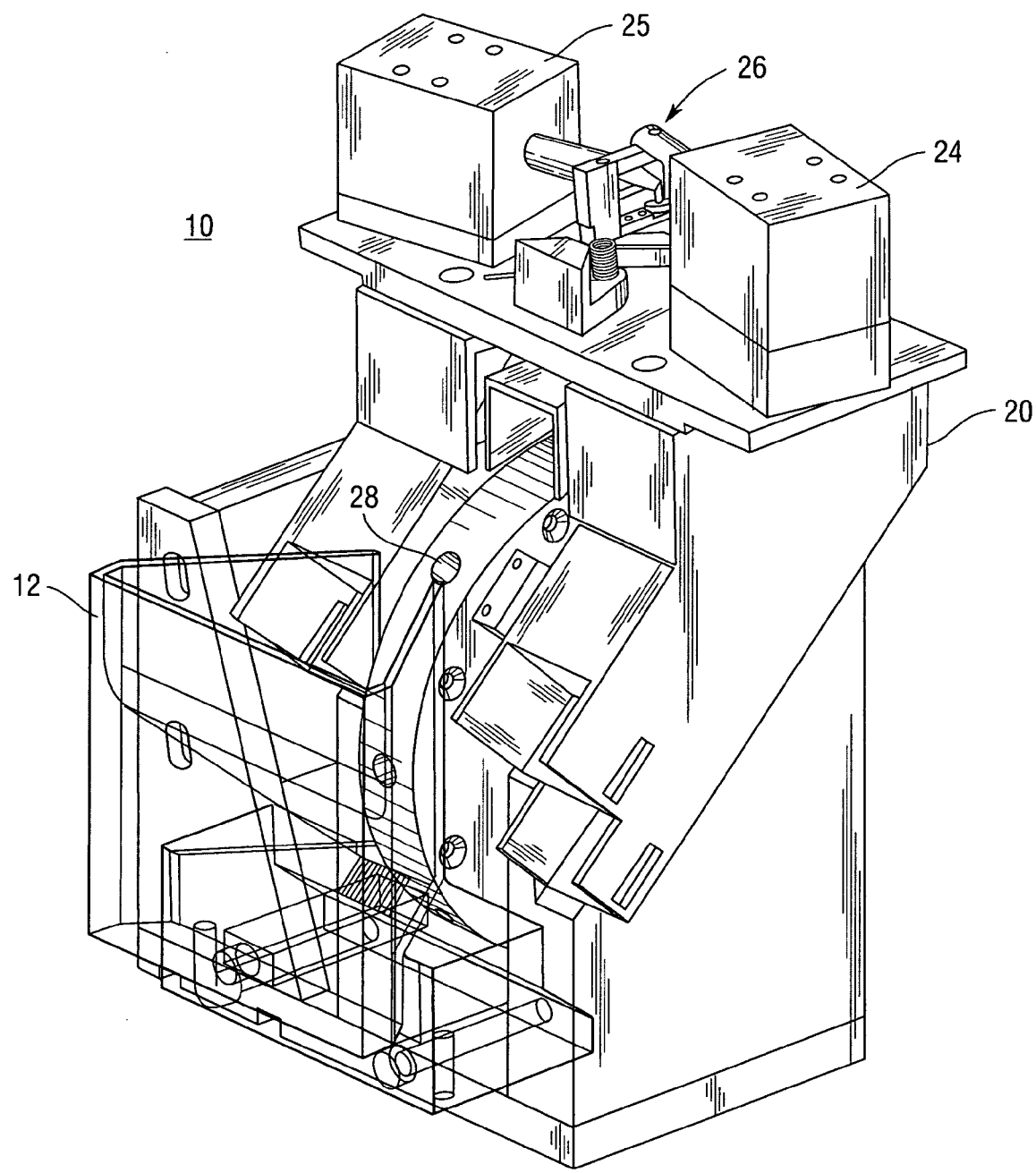
FIG. 1 illustrates one embodiment of a singulating device and counter based thereon, together with portions of a hopper (shown in phantom) containing items to be singulated and counted, constructed according to the teachings of the present disclosure.
Figure 2A:
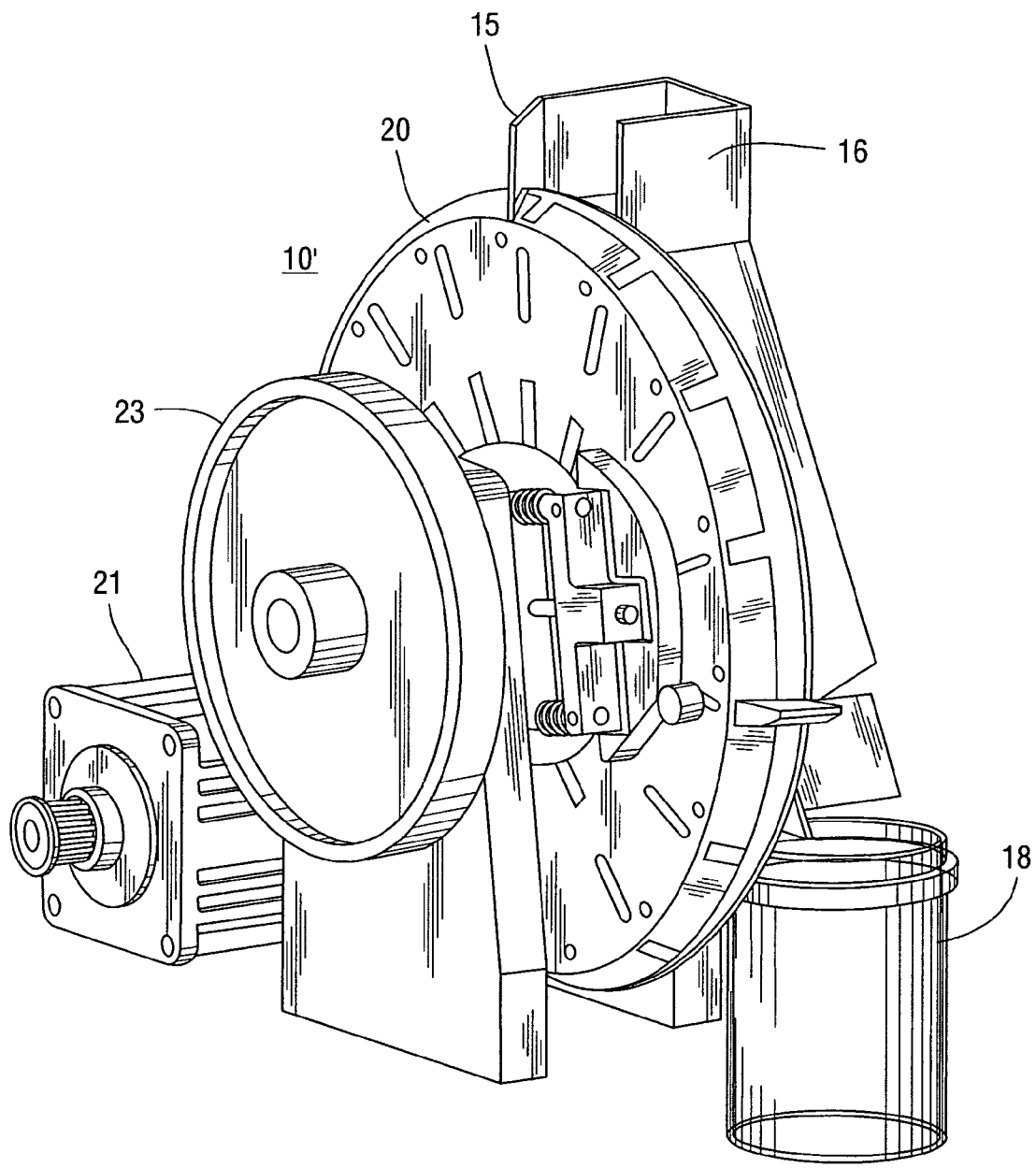
Figure 2B:
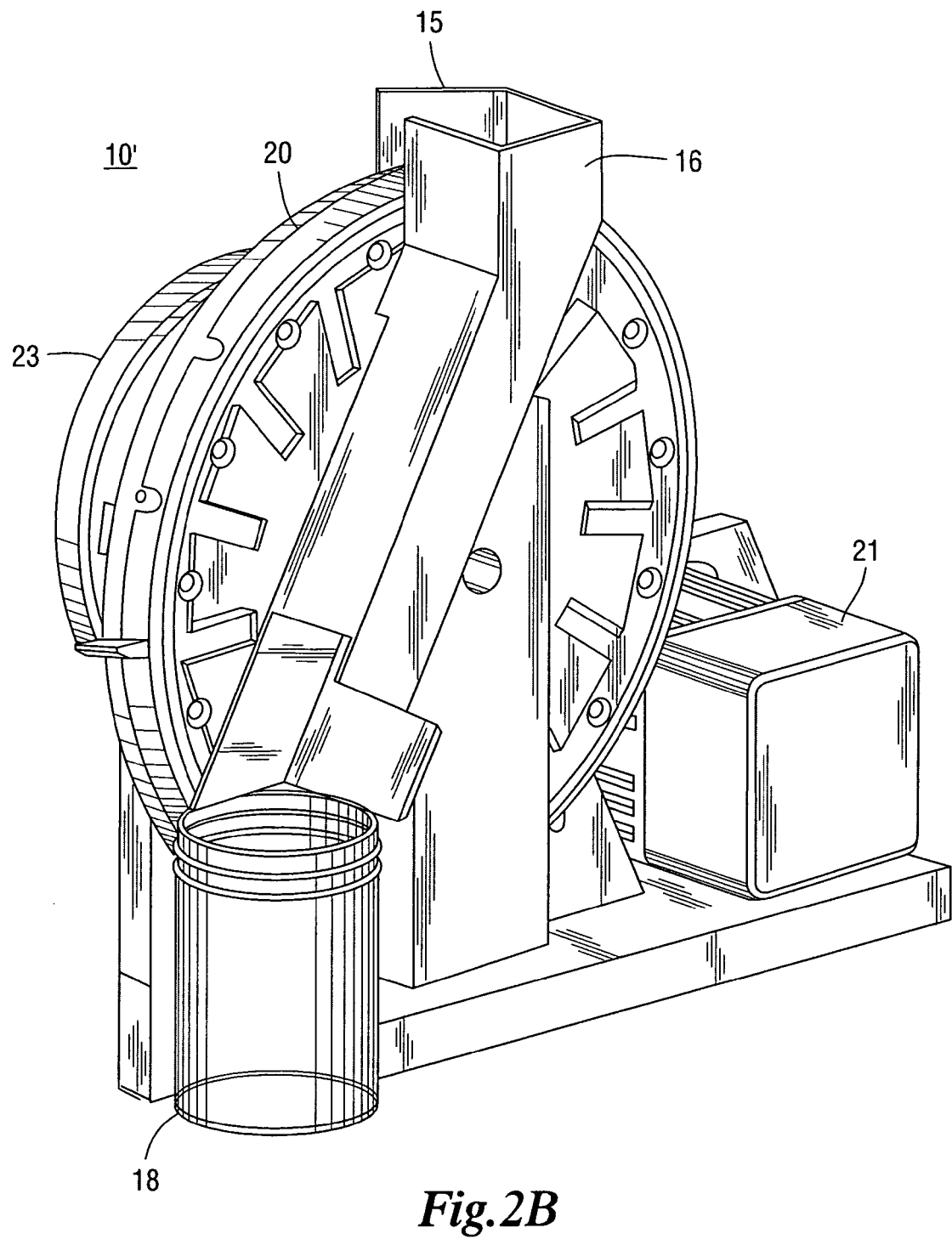

FIG. 1 illustrates one embodiment of a singulating device and counter 10 constructed according to the teachings of the present disclosure. The singulating device and counter 10 is used in conjunction with a removable hopper 12, a portion of which is shown in phantom in FIG. 1. Another embodiment of a singulating and counting device 10', with the outer housing and hopper removed, is illustrated in FIGS. 2A and 2B. In FIGS. 2A and 2B, a scraper 15, a main or dispensing path 16 and an end user container, e.g. vial 18, are also shown. Seen in both FIGS. 1, 2A and 2B is a hollow, rotatable singulating disc 20 having a plurality of openings around the periphery thereof. Two versions of the disc 20 are illustrated, one in FIG. 1 and the other in FIGS. 2A and 2B. The reader should be aware that the profile of disc 20, i.e. the shape around the periphery when viewed from the side, may take several shapes, e.g. flat, curved (convex or concave), etc. or some combination, e.g. convex portion tapering to a flat portion.

Figure 2C:
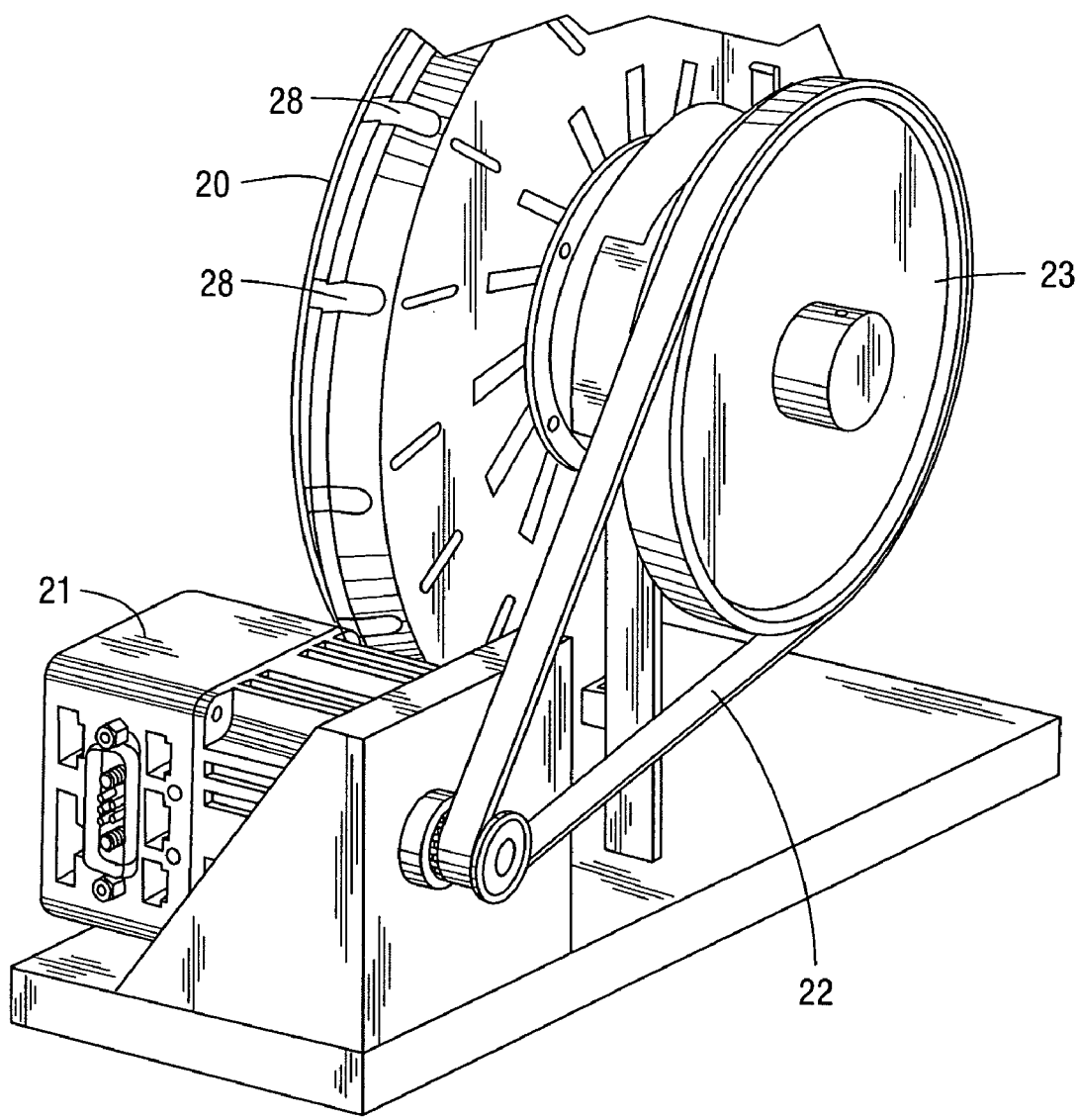
FIG. 2C illustrates the belt drive for the singulating disc.
Figure 3:
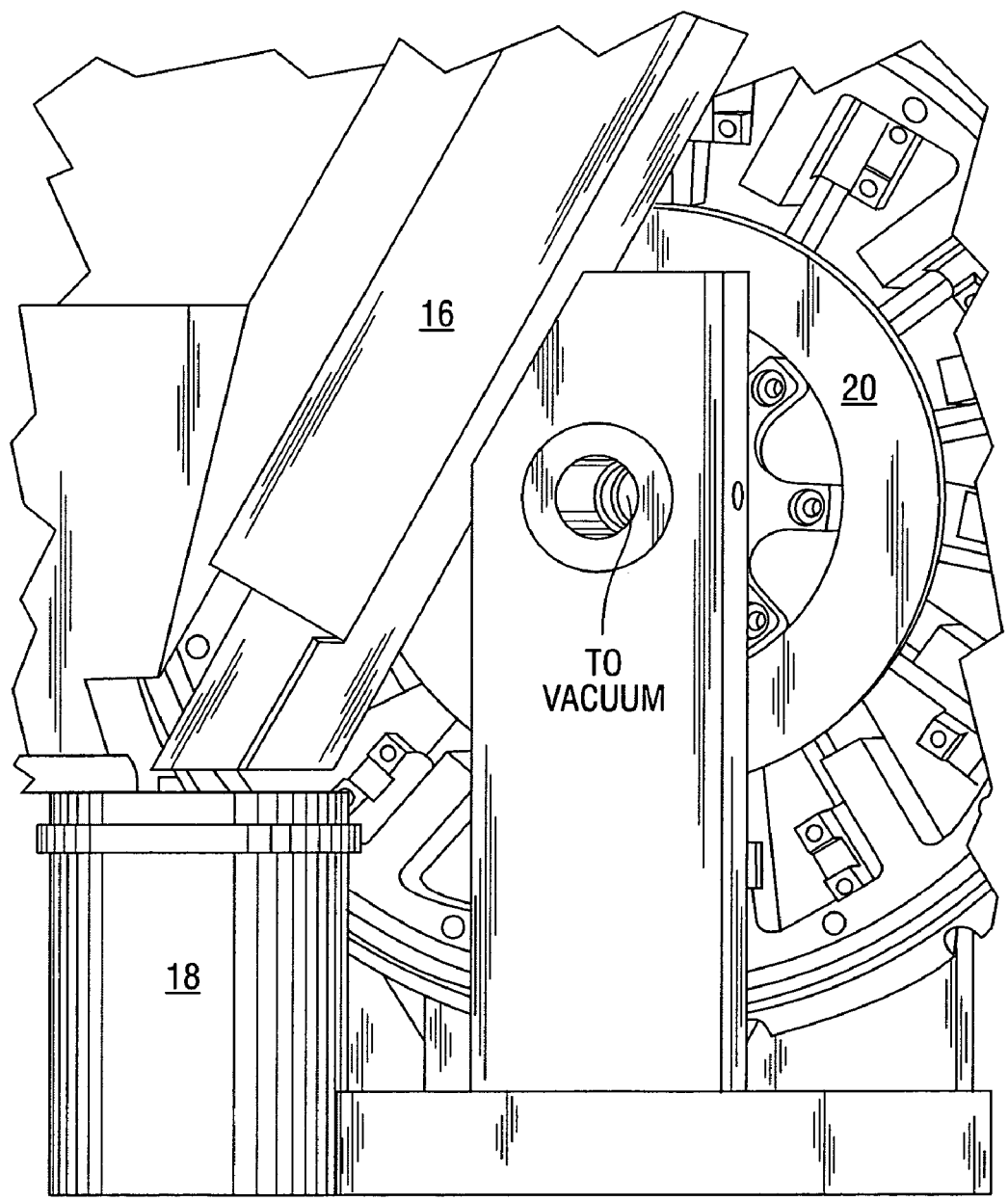
FIG. 3 illustrates the stationary air shaft.

Shown in FIGS. 2A and 2B is a source of rotary motion, such as motor 21, coupled to the singulating disc 20 by a belt 22, shown in FIG. 2C, via a pulley 23 and shaft (not shown). A vacuum source (not shown) is also coupled to the singulating disc 20 as shown in FIG. 3. For embodiments having more than one singulating disc, which embodiments are discussed in greater detail below, a single vacuum source may be used. By using more than one singulating disc, system throughput (items singulated and dispensed per second) is increased; a variety of different items could be dispensed (one type per singulating disc) without needing to add multiple vacuum sources. The present disclosure focuses on the singulating and counting of medicaments (pills, gel caps, tablets, etc.) although other items could be singulated, such as seeds, candy, etc. and, optionally, counted. Because the dispensing of medicaments is often done based on a prescription, counting often accompanies singulation, although singulation could be performed without counting. Further, dispensing of singulated, counted medicaments is usually performed in conjunction with a bottle or vial, although singulated items, counted or uncounted, could be dispensed to a movable belt or other device for further processing or for transport to another location, e.g. singulated candy moved to a wrapping station.

Referring back to FIG. 1, the singulating disc 20 has a portion thereof, substantially around the 7 to 9 o'clock position, which rotates through the removable hopper 12. Also shown in FIG. 1 is a first solenoid 24 and a second solenoid 25 which act upon a spring-loaded diverter 26 located at approximately the 11-12 o'clock position on the singulating disc 20. The operation of the spring loaded diverter 26 is discussed in greater detail in conjunction with FIGS. 6 and 7 below.

In operation, the device for singulating and counting 10 uses negative pressure to singulate and count a multitude of differently shaped and sized pills without requiring calibration for each shape and/or size. The hollow singulating disc 20 is vertically carried by the housing. The disc has a number of holes or openings 28 around its periphery. A vacuum is pulled though the holes by a pump which is connected to a hollow shaft, which is connected to the inside of the hollow singulating disc 20. Pills placed in the hopper fall, via gravity, to the bottom of the hopper to contact the periphery of the spinning disc substantially in the 7 to 9 o'clock position. The vacuum available at each of the holes causes a pill to attach which is held there while the disc rotates the pill upwards in a clockwise direction as seen in FIG. 1. At the top, approximately the 11 to 12 o'clock position, the spring-loaded diverter 26 may direct the items off the disc 20 into one of two paths, discussed below, depending on the result of an inspection, e.g., fragment detection, pill identification/verification, etc., a counter or other type of control device, or may allow the items to remain on the singulating disc 20. Items that make it past the spring-loaded diverter 26 are removed by scraper 15 so as to fall into dispensing path 16.

In one embodiment, the singulating disc 20 is six inches in diameter and 0.85 inches thick. The majority of the inside of the disc is hollow. Threaded channels that interface with nozzles may be equally spaced around the disc. Another embodiment uses fifteen holes equally spaced around the disc 20. The vacuum is drawn through the hollow disc and the nozzles to provide the suction for attracting and conveying the pills. The hole size is selected so that only one of the smallest of items anticipated to be dispensed will fit on a hole, while the vacuum is sized so that there will be sufficient force to pick up the largest of items anticipated to be dispensed. Alternatively, if the holes are larger than the smallest item to be dispensed, such large holes may be provided with a screen or bars to prevent small items from being entrapped within the hole. Depending upon the formulary to be dispensed, there may need to be more than one singulating disc 20 to handle the entire formulary.

The disc is attached to two shafts, one of which rests on radial bearings. That shaft is attached to motor 21 (via the pulley 23 and belt 22 mentioned above) which provides a source of rotary motion for causing the disc 20 to rotate. The disc may be attached to the motor 21 via the timing belt 22 and pulley 23 in a 7:1 ratio. That eliminates the need for a gearhead on the motor and will reduce the overall dimensions of the system. Of course, a gearhead may be used on the motor 21 to achieve an even larger ratio. The other shaft is hollow and interfaces with a vacuum source as shown in FIG. 3.

One embodiment of the present disclosure uses a singulating disc 20 having fifteen holes drilled directly into the radial edge of a solid disc to thereby produce the "hollow" disc. In such on embodiment, the threaded nozzle inserts are not used. Whether nozzles are or are not used, the profile of the disc may be sloped as seen best in FIGS. 2A and 2B so as to eliminate any stray items from resting on top of an item attached as a result of the application of the vacuum. If an item is not directly attached as a result of the vacuum, it will slide off the edge and remain within the hopper. A rubber surface may also be added to increase the friction between the items and the disc. A rubber, or other similar surface, will help to keep the items attached while the disc is rotating.

Figure 4:
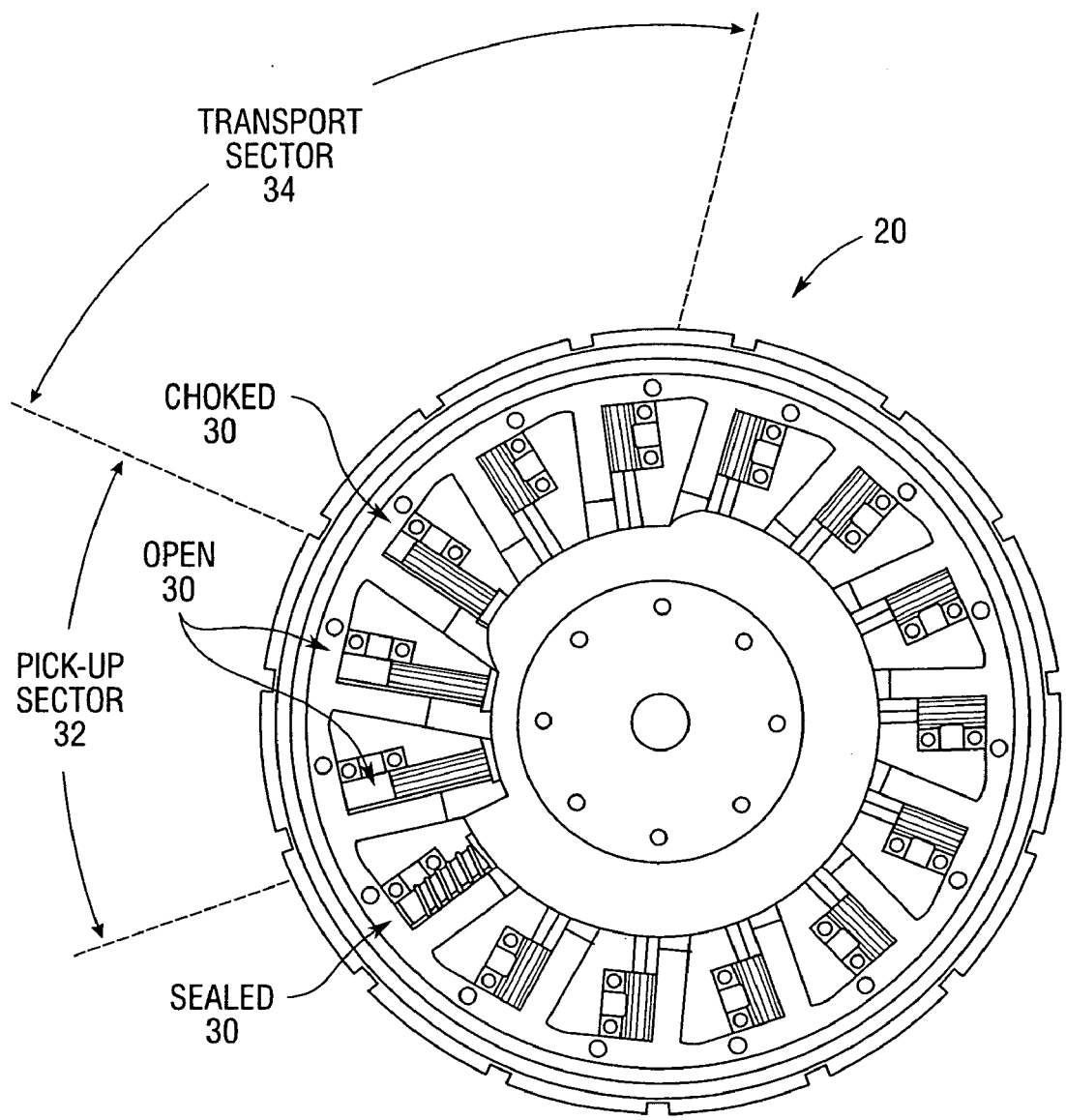
FIG. 4 illustrates a vacuum management system carried internally by the singulating disc.

FIG. 4 illustrates a vacuum management system carried internally of the singulating disc 20. In one embodiment, a plurality of spring-loaded pistons 30 is provided, with four being illustrated in FIG. 4. All of the pistons 30 are responsive to a cam 36. Each piston 30 is slightly smaller in diameter than its corresponding vacuum hole. There are three disc rotation sectors that should accomplish different purposes with respect to the items. The "pick-up" sector 32 is the region where the items become attached to the disc. The pick-up sector 32 needs full vacuum to accomplish that purpose. Hence, the pistons 30 are fully retracted and full flow is achieved through the open vacuum hole. A second sector is the "transport" sector 34. This is the section where the items are held in place, and conveyed from the hopper to the diverter 26 and the scraper 15. The transport sector 34 does not need as much flow rate as the pickup sector 32 because all it has to do is hold an item on the disc rather than causing the item to attach in the first instance. The pistons 30 are inserted part way into the holes at this point, thereby restricting or choking air flow and conserving the air flow for the pick-up sector 32. The third and final sector covers the remainder of the disc which is referred to as the "sealed" sector. That is the portion of the disc from approximately the 12 o'clock position to the 7 or 8 o'clock position. This is the region where the items have been removed by either the diverter 26 or the scraper 15 such that the holes are simply rotating back towards the hopper. This region requires no airflow and hence the pistons are moved to a location so as to completely seal the holes. Various surfaces of the cam 36 may provide the forces against the spring forces of the pistons 30 needed to move the pistons 30 to positions where they seal or choke their respective hole. When the force provided by the cam 36 is absent or minimal, the springs move the pistons 30 to a position where their respective hole is fully open.

Figure 5:
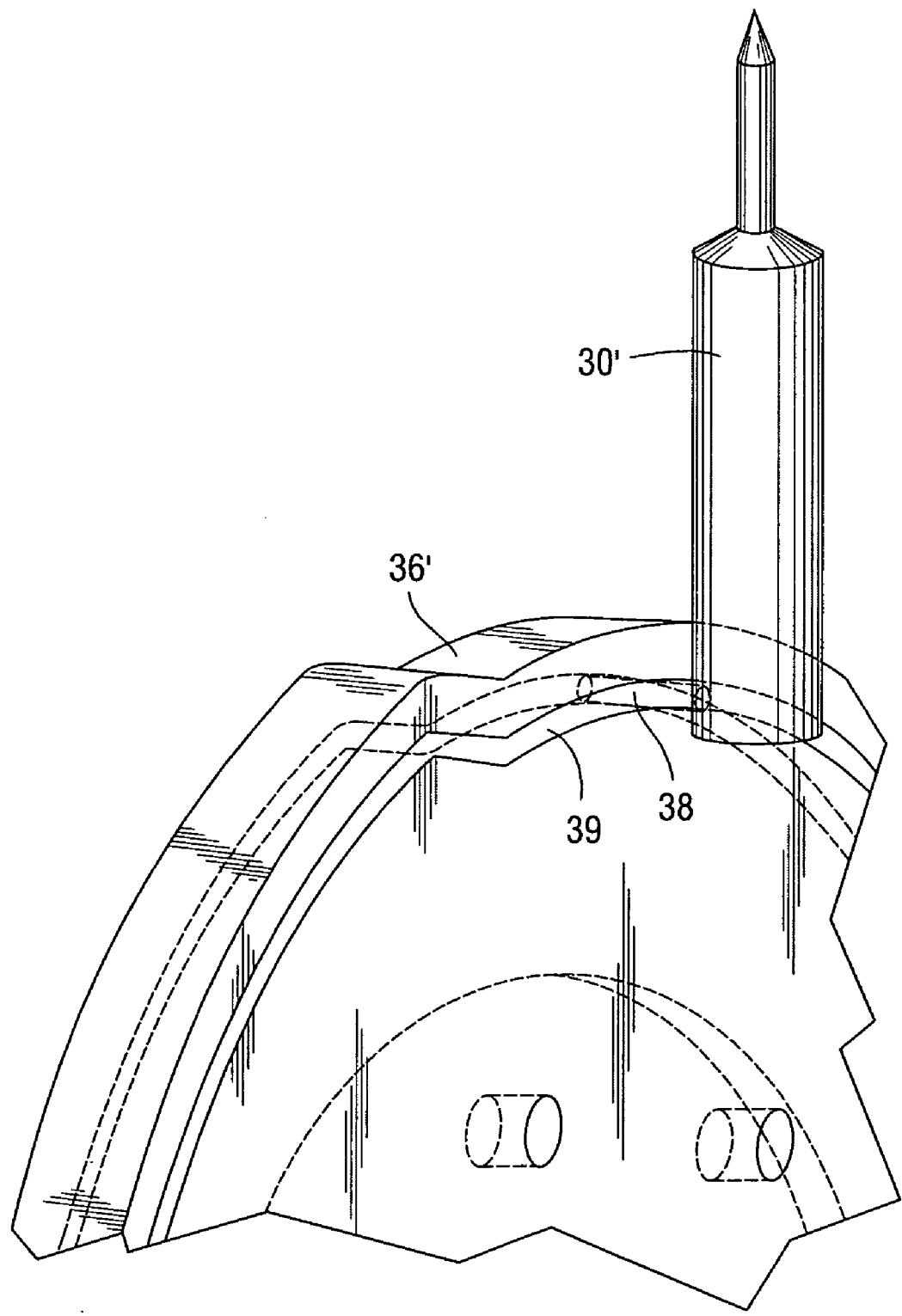
FIG. 5 illustrates another control mechanism for the vacuum management system.

As an alternative to the spring loaded pistons 30 of FIG. 4, FIG. 5 illustrates an embodiment in which each piston 30' may have a pin 38 which rides in a groove 39 of cam 36'. In such an embodiment, the springs may be eliminated as the pins 38 riding in groove 39 provide the necessary motion for the pistons 30'.

Figure 6:
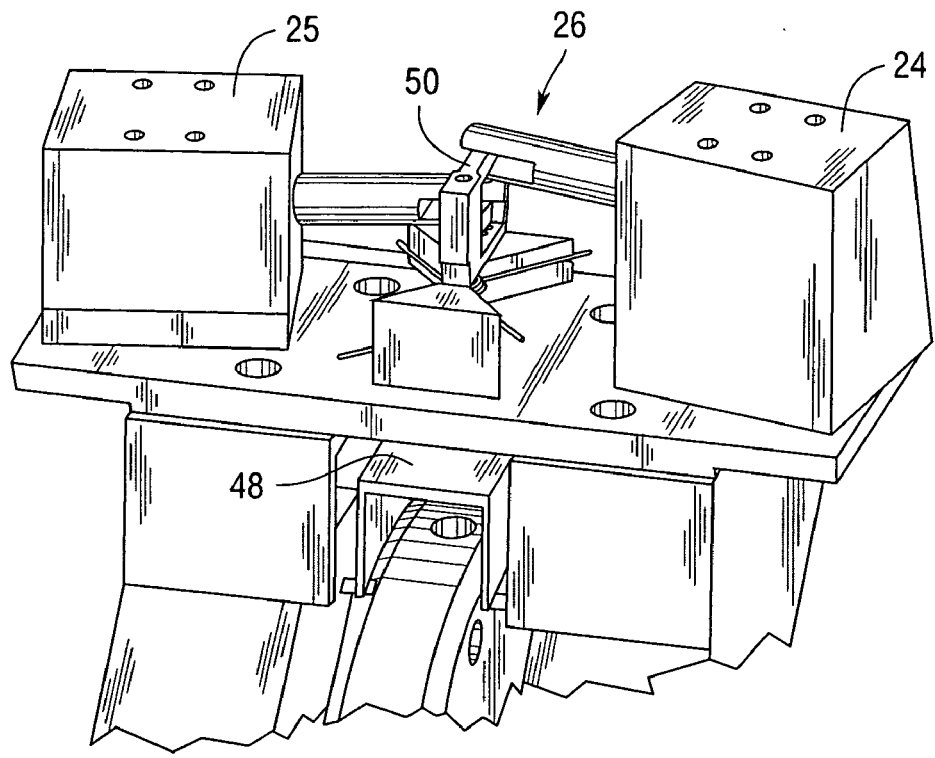
FIGS. 6 and 7 illustrate two positions for the diverter shown in FIG. 1.
Figure 7:
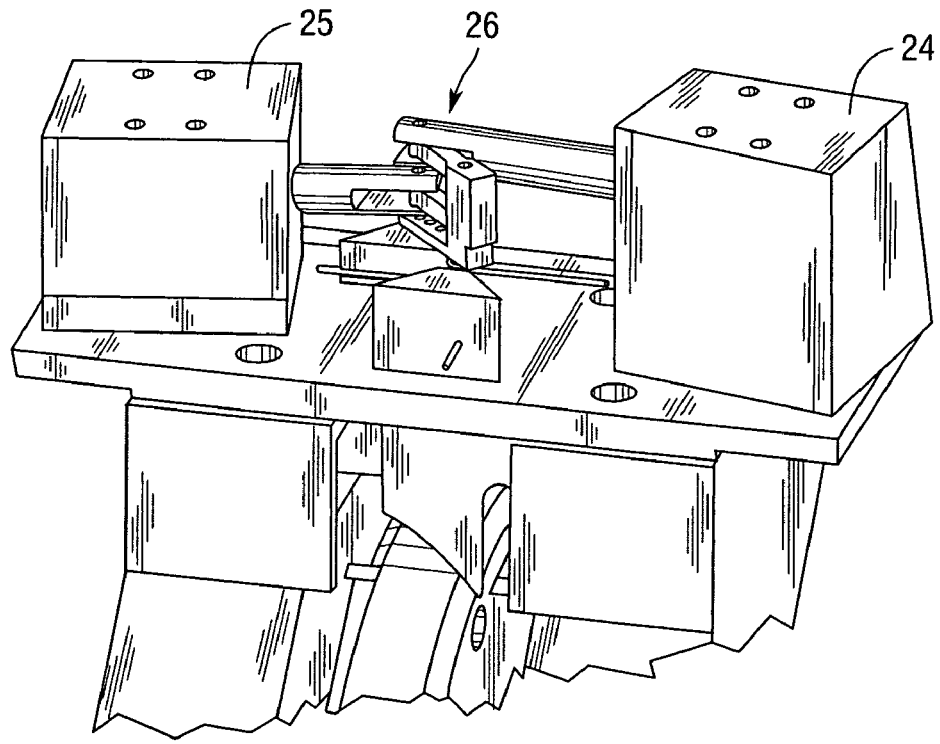
Figure 13A:
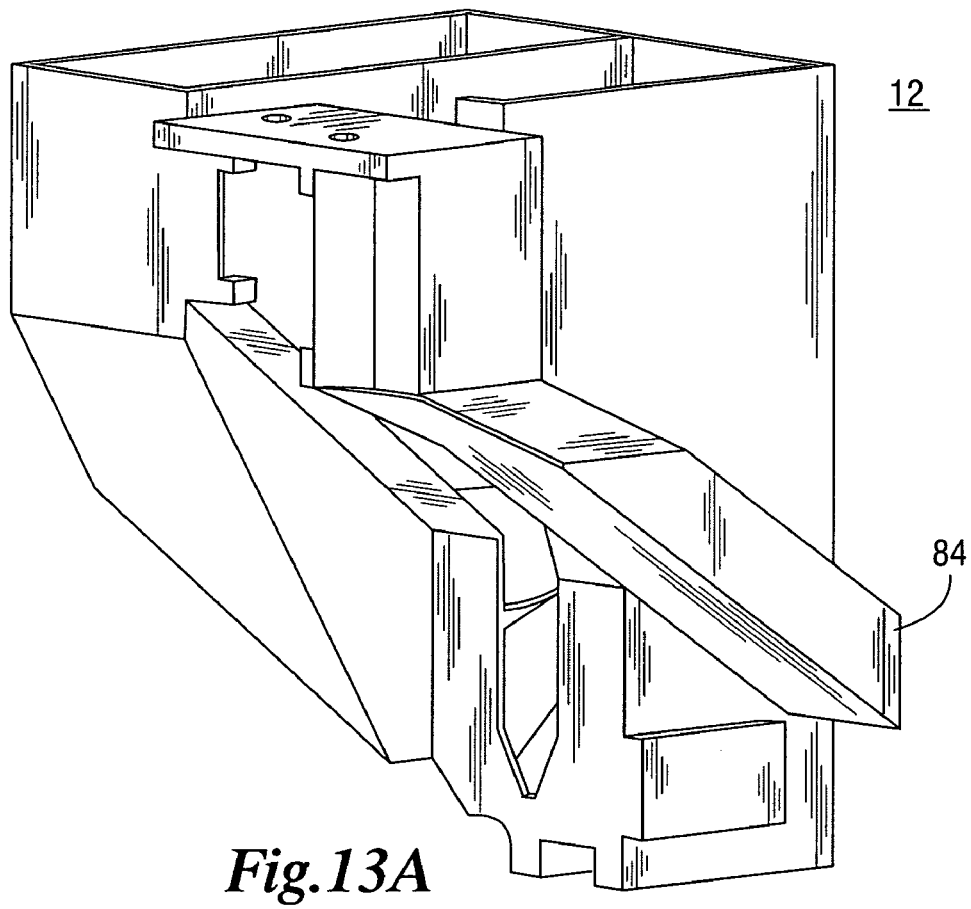
FIGS. 13A, 13B and 13C are various views of a hopper used in conjunction with the present disclosure.
Figure 13B:
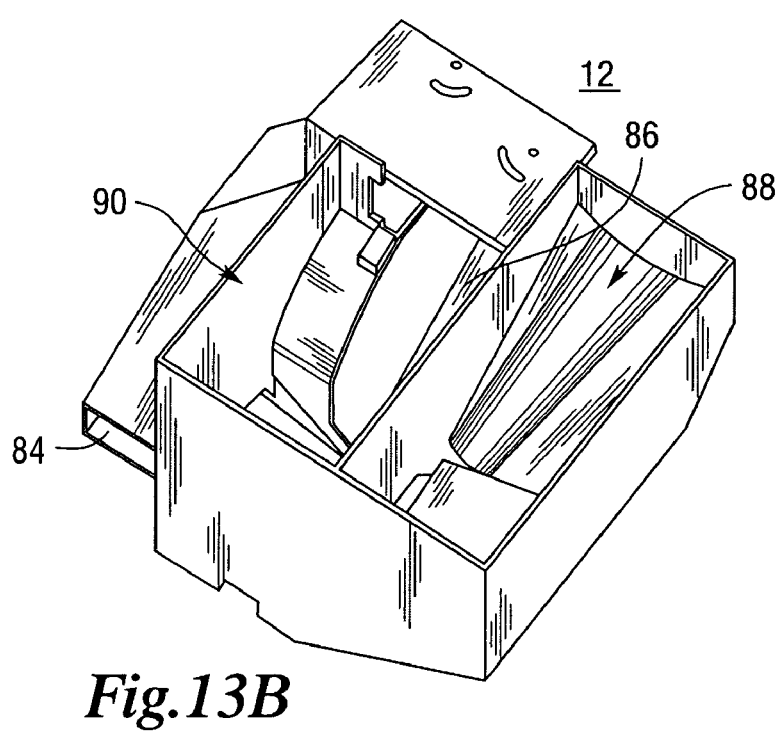
Figure 13C:
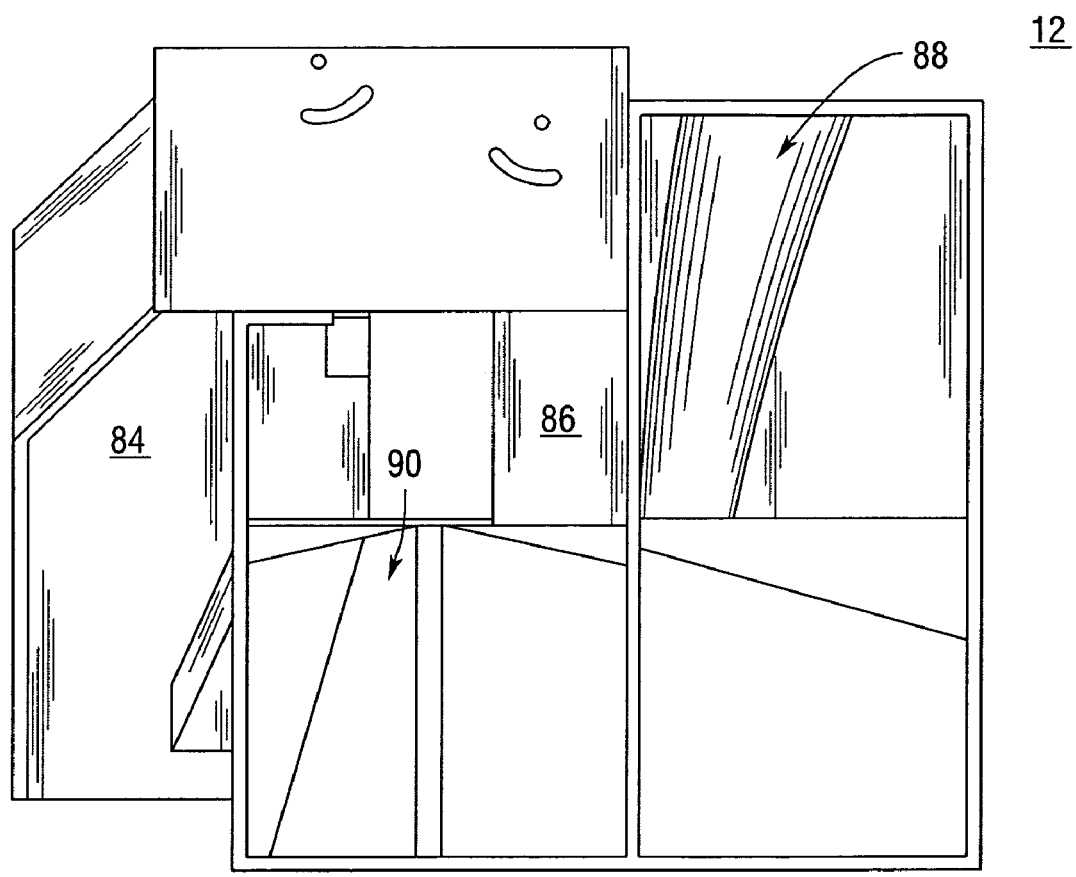

Turning now to FIGS. 6 and 7, after an item is picked up, it will travel past a fragment detector or other type of inspection device (which may also be used for counting) that will determine the path to which the item will be directed. Three paths are provided for directing items removed from the singulating disc 20. The dispensing path 16 (see FIG. 2) directs items to the vial 18, other patient container, or a conveyor belt (not shown) among others. A reject path 84, shown and discussed below in conjunction with FIGS. 13A-13C, is provided so that items which are incomplete (fragments), incorrect, or otherwise inappropriate, may be gathered for discarding or return to the manufacturer. Finally, a return to hopper path 86, also shown and discussed below in conjunction with FIGS. 13A-13C, is provided so that items may be returned to the hopper 12.

Direction of the item into the proper path is accomplished in part by the spring-loaded diverter 26 which is operated in conjunction with the solenoids 24, 25. The diverter 26 may be comprised of a U-shaped member 48 connected to a spring loaded, dowel pin pivot 50 to which the solenoids 24, 25 are connected. When neither of the solenoids is energized, the springs place the U-shaped member 48 in a position parallel with the disc as seen in FIG. 6. That permits items to pass through the diverter 26 so as to be wiped off of the disc 20 by scraper 15 into the main path 16. When one or the other solenoid is energized, the energized solenoid overcomes the spring force and rotates the diverter 26 to an angle so that it diverts items into either the reject path 84 (seen in FIG. 13) or the return to hopper path 86 (seen in FIG. 13) depending upon which of the solenoids 24, 25 is energized.

Figure 8:
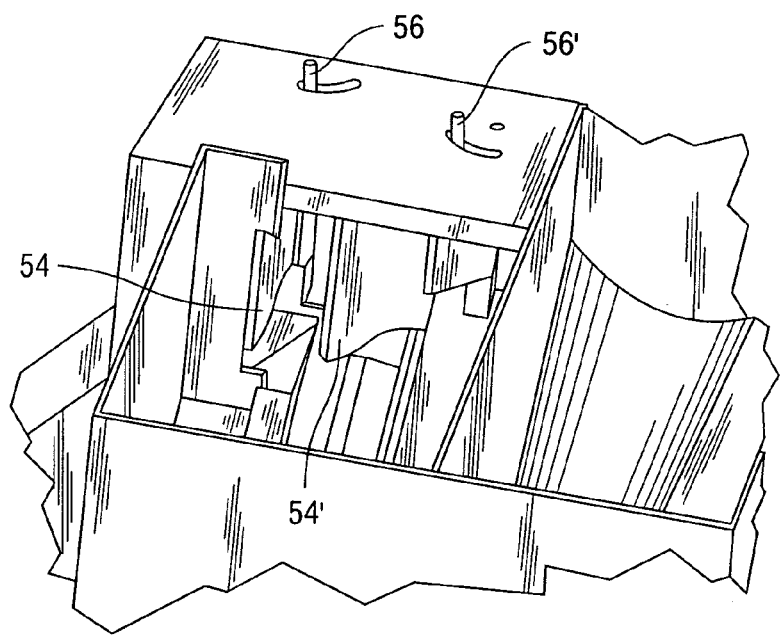
FIG. 8 illustrates an alternative embodiment to using the solenoids and U-shaped member of FIGS. 6 and 7.

Another embodiment of the diverter 26 is illustrated in FIG. 8. The embodiment shown in FIG. 8 uses two separate "doors" 54, 54' that swing over the edge of the disc 20 via a control pin 56, 56', respectively, connected to the doors. The pins 56, 56' could be actuated by a cam that could control the doors 54, 54' with one motor input. Other types of mechanical, electrical and pneumatic diverters may be designed that provide the function of allowing an item to pass, or diverting the item to one side or the other side of the disc 20. For example, nozzles (connected to a supply of compressed air or other gas) may be provided on either side of the singulating disc 20 to blow items into one path or the other. All such alternatives that divert an item to one side or the other of disc 20 or allow and item to pass are within the scope of the present disclosure.

The disclosed diverters are one type of means for removing. Clearly, the type of means for removing actually used in any particular embodiment will depend upon the purpose of the singulating and/or counting and the number of paths involved. In a situation where there is only a single path, the means for removing may be a simple blade, scraper, or the like. Where more than one path is involved, a more complicated means for removing such as a diverter and/or a diverter in combination with a blade or scraper may be provided. All such variations of devices and combinations of devices are intended to be included in the phrase "means for removing".

Figure 9:
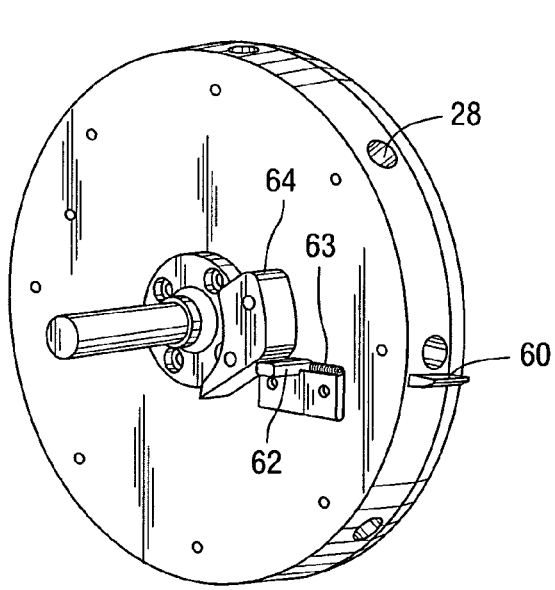
FIGS. 9 and 10 illustrate two embodiments for a cam actuated stirring system.
Figure 10:
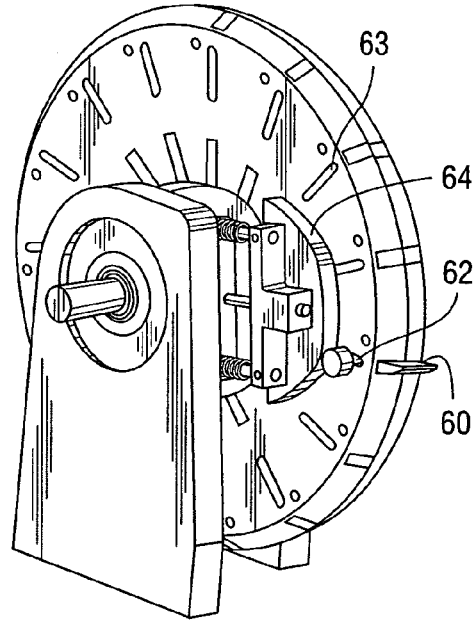

Due to the problem of large items becoming interlocked and "bridging" in the hopper, a mechanism to mechanically agitate the items is incorporated into the singulating disc 20. Two versions of the design are illustrated in FIGS. 9 and 10. The design comprises a paddle 60 that is spring loaded and normally recessed into the periphery of the disc under each nozzle or opening. The paddle is connected to a shaft, pin or other device 62 extending through a slot or opening 63 in a side of the disc. The pin 62 acts as a cam follower. The cam follower interfaces with a paddle control cam 64. As the disc rotates, the paddle control cam 64 interfaces with the pin 62 at the moment when the particular nozzle or opening is facing the surplus of items within the removable hopper. The cam, acting upon the pin 62, causes the paddle 60 to extend into the items and agitates the items. That agitation breaks any bridging or interlocking of the items and helps to lift an item onto a nozzle or opening. As the disc rotates, the item will become attached to the nozzle or opening due to the vacuum. After the item is attached or captured, the surface of the paddle control cam 64 allows the paddle 60 to recess back into the disc so as not to interfere with the operation of the diverter 26.

Figure 17A:
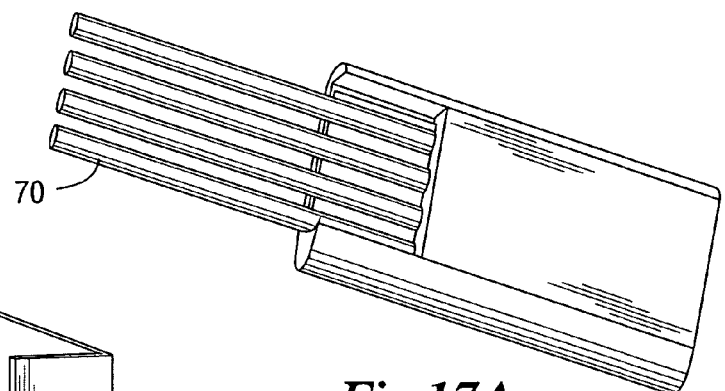
FIGS. 17A, 17B and 17C illustrate a paddle configuration comprised of pins.
Figure 17B:
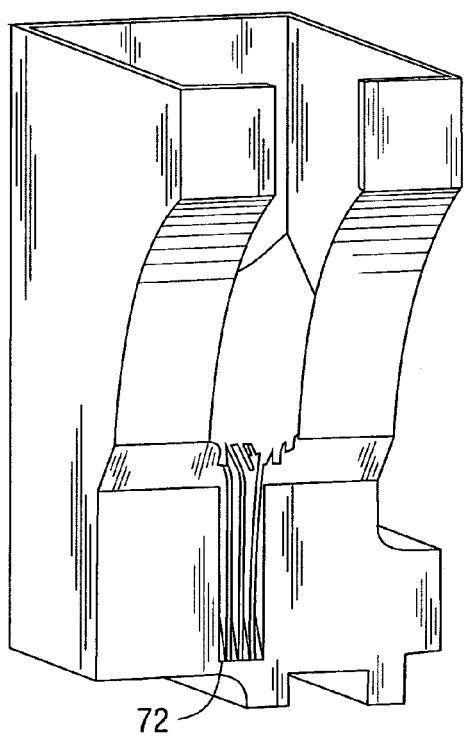

FIG. 17A illustrates a paddle design involving pins 70. The advantage to designing the paddle so as to have pins 70 is that the pins 70 can now be extended before the corresponding hole in the singulating disc enters the pickup chamber. If the pickup chamber is designed with mating channels 72, see FIG. 17A, the pins 70 can be extended before they enter the pickup chamber of the hopper.

Figure 17C:
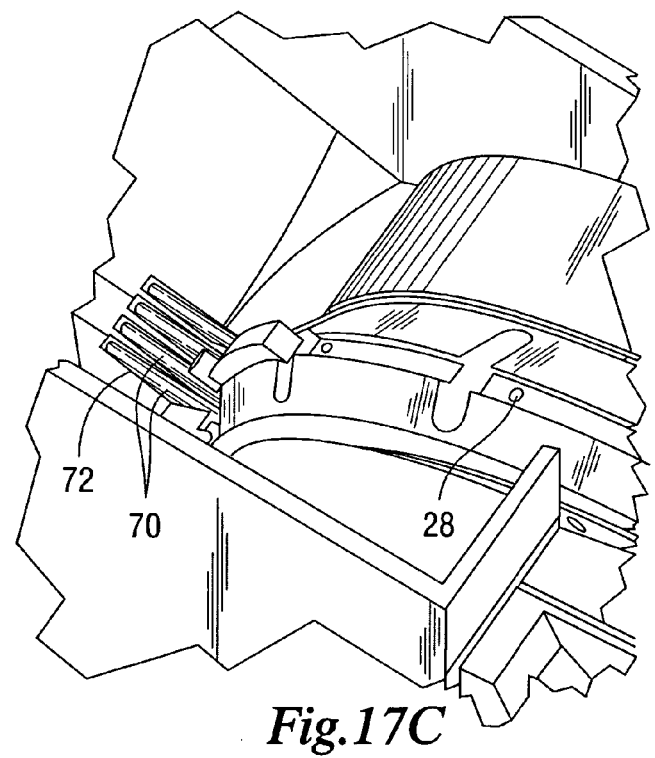

When the pins 70 enter the pickup chamber (see FIG. 17C) they will be fully extended and will lift an item from the bottom rather than scooping it from the side. That action provides more reliable pickup and eliminates the paddle being extended into a mass of items that restricts motion. That action also eliminates the need for precise mating of the hopper to the housing and disc and ensures that the paddles are extended at the exact moment that they enter the pickup chamber. Note that the pin paddle could be designed with any number of pins 70 greater than one. A four pin configuration is shown in the figures for purposes of illustration and not limitation.

Figure 16A:
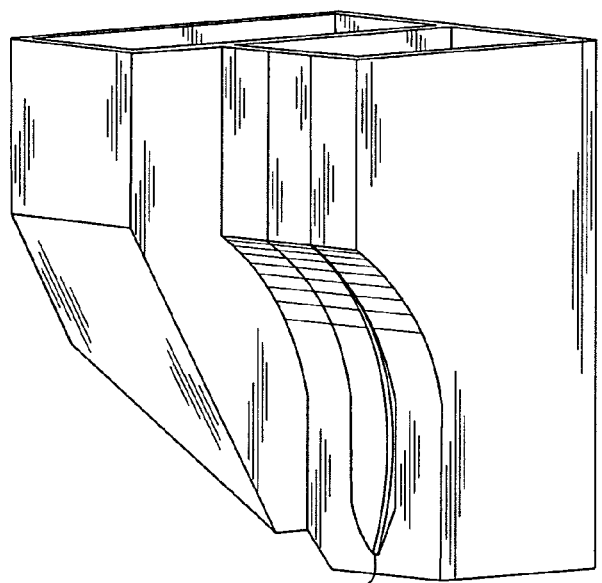
FIGS. 16A and 16B illustrate a hopper door in a closed and in an opened position, respectively.
Figure 16B:
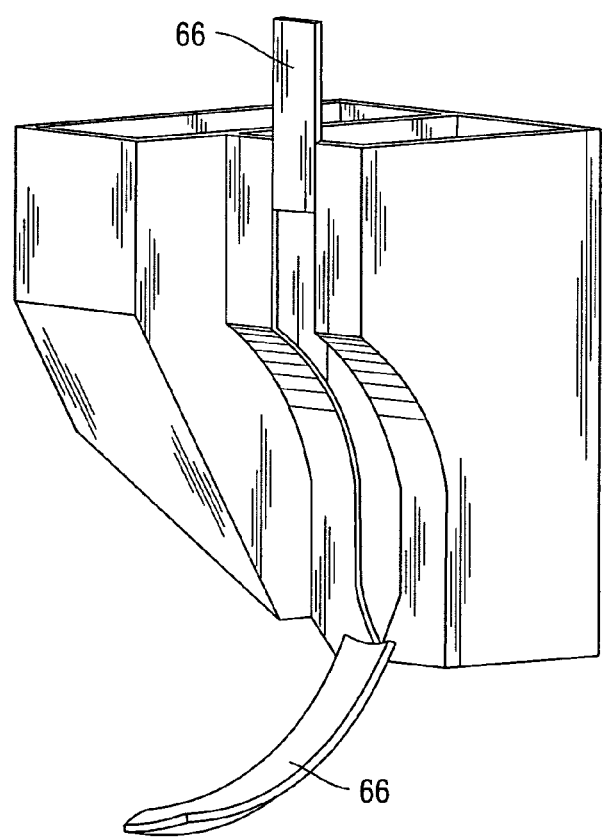

It has been determined that all of the paddles 60 need to be retracted from all positions on the disc 20 for removal of the hopper from the device 10. To remove the hopper from the disc, a two part door 66, or pair of doors, seen if FIGS. 16A and 16B, closes against the disc 20 to separate and remove all items from the disc 20. Therefore, when the hopper is removed, the items don't spill out of the device 10. However, for the door 66 to close against the disc and separate uncounted items from it, the profile of the disc must be a smooth, constant profile. Any paddles extending from the periphery of the disc would interfere with the door 66. Therefore, all paddles 62 must be retracted before the hopper is removed.

Figure 11:
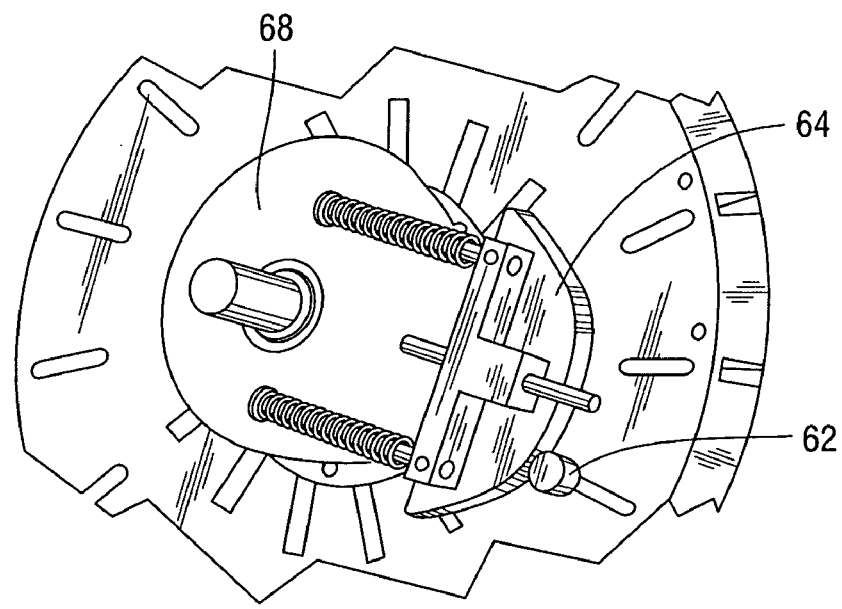
FIG. 11 illustrates a cam used to inactivate the stirring system of FIGS. 9 and 10.

Turning to FIG. 11, FIG. 11 illustrates a cam 68 that may be used to inactivate the stirring system of FIGS. 9 and 10. The cam 68 controls the position of the paddle control cam 64. When the user wants to remove the hopper, rotation of the cam 68 by 180° will cause all of the paddles to retract as the paddle control cam 64 will be moved to a position in which it cannot interface with any of the pins 62. Thus, removal of the hopper may be facilitated. Rotating the cam 68 by another 180° will again place paddle control cam 64 in a position so as to operate those pins 62 which come into contact therewith.

Figure 12:
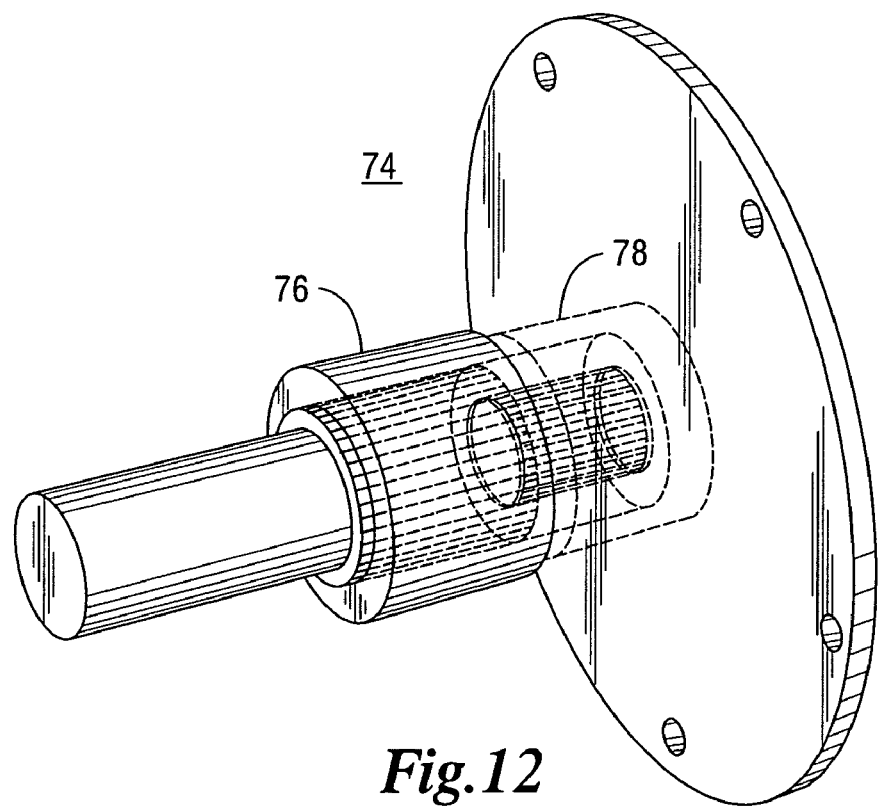
FIG. 12 illustrates an input splitter so that one source of rotary motion can be used to rotate the singulating disc and control the position of a cam.

It is desirable that the input remain a single motor input and that a separate input for paddle retraction not be added. That can be accomplished by using an "input splitter" 74 as shown in FIG. 12. The input splitter separates the motor input into two separate inputs which rotate in different directions. That may be accomplished using two roller clutches 76, 78. Roller clutches are off the shelf devices that transmit torque in one direction while rotating freely in the other. By using two of these roller clutches that transmit in opposite directions, the input can be split. When the motor rotates one way, it transmits rotary motion to one shaft through one clutch 76 while the other clutch 78 rotates freely. When the motor rotates in the opposite direction, the torque is transmitted via clutch 78 to another shaft while the clutch 76 rotates freely. By controlling the rotation of the disc with the one shaft and position of the cam 68 with the other shaft, the paddles can be retracted using the same motor that is used to rotate the disc 20 by simply causing the motor to rotate in the opposite direction.

The hopper 12 is shown in detail in FIGS. 13A-13C. The hopper 12 houses a surplus of items in a storage chamber 88 and directs them, via gravity, toward a pickup chamber 90 through which the singulating disc 20 rotates. The storage chamber 88 and pickup chamber 90 are contoured so the items will fall to the bottom of the pickup chamber 90 and be place in close vicinity, or touching, the periphery of the singulating disc 20. Positive pressure may be injected into the bottom of the hopper 12 to agitate the items and provide extra force to attach them to the vacuum holes. The hopper 12 may contain one or more baffles to reduce the volume of items in the pickup chamber 90 and hence the force on the items being picked up in the pickup chamber. That will eliminate a multitude of items resting on the bottom items which are interfacing with the vacuum holes. As a result of the baffle, the level of items in the pickup chamber 90 will be lower than that of the storage chamber 88, which will aid in pickup efficiency.

Figure 14A:
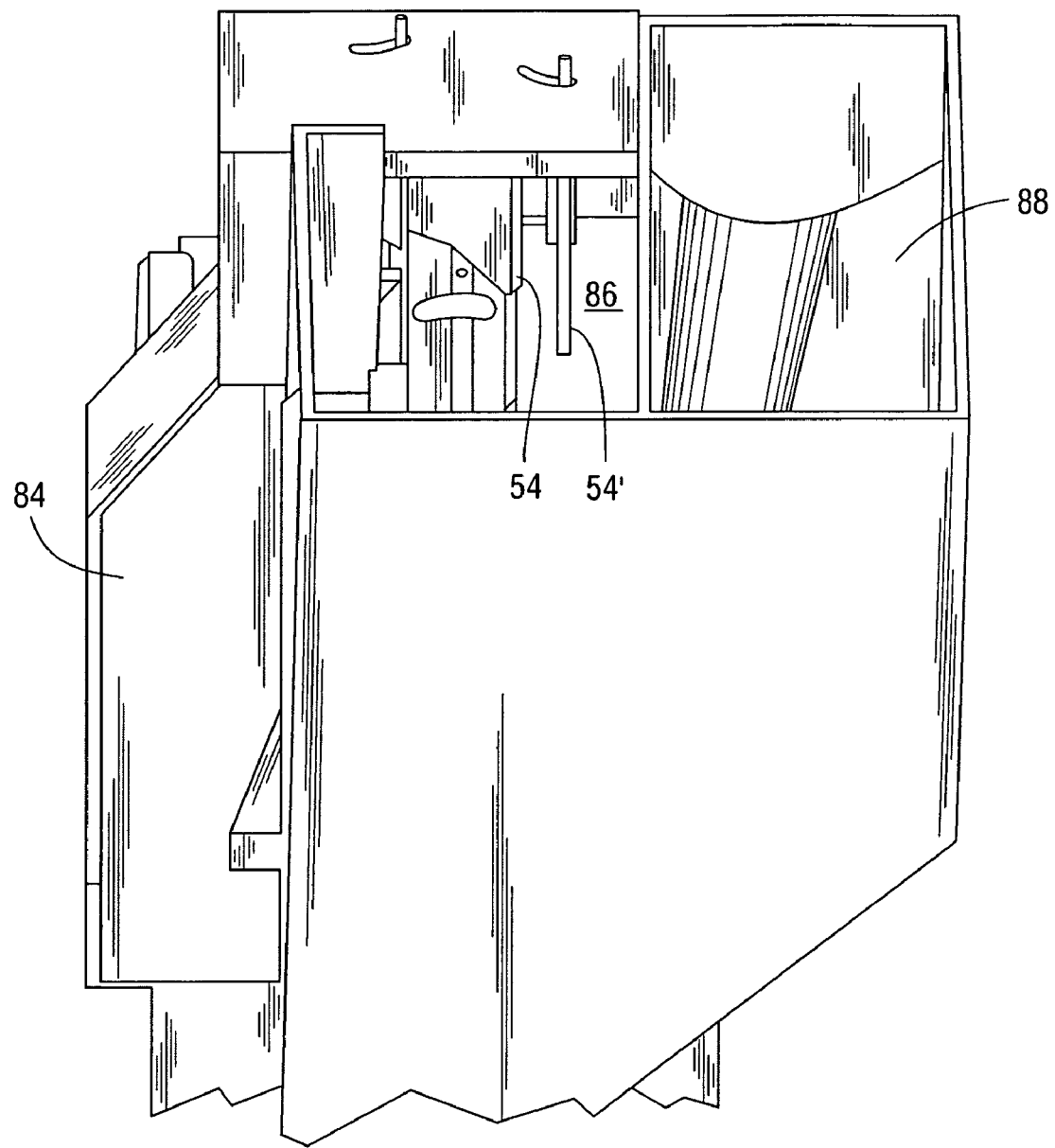
FIGS. 14A and 14B illustrate the hopper of FIG. 13 in place in the counting and singulating device of the present disclosure.
Figure 14B:
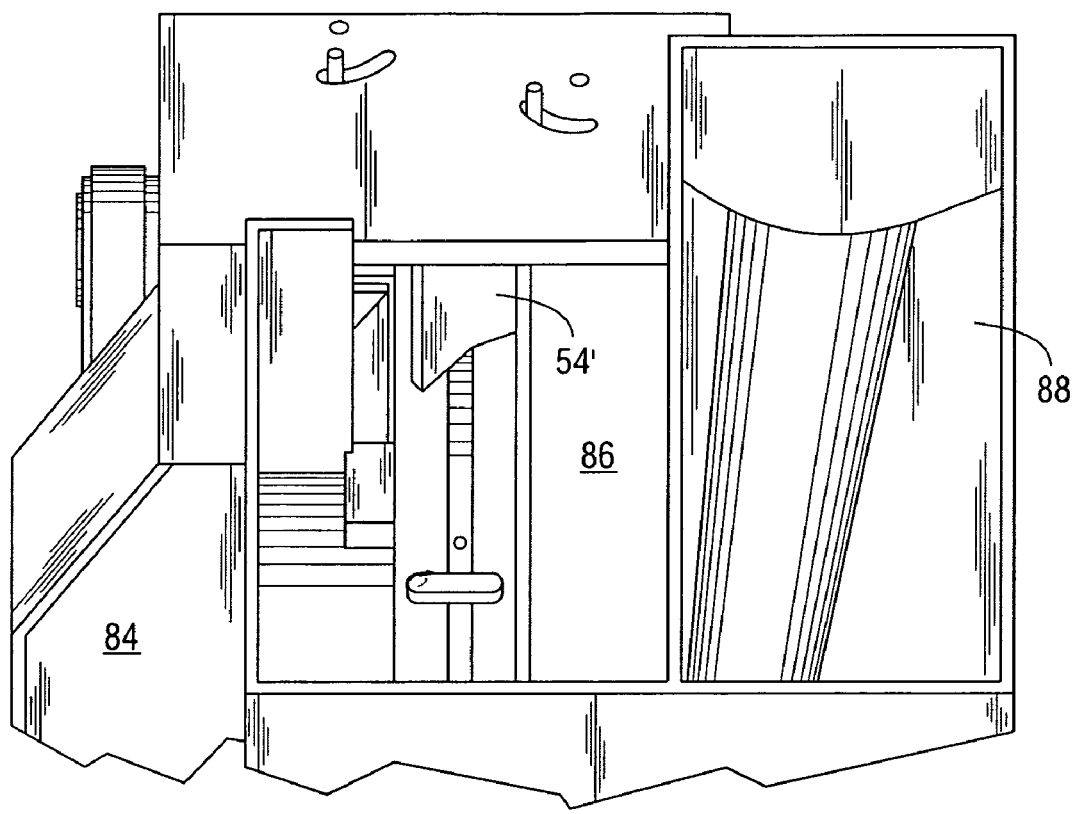

FIGS. 14A and 14B illustrate the hopper 12 interfacing with the singulating disc 20. In this embodiment, doors 54, 54' are carried by the hopper 12 and form the diverter 26. Door 54 diverts items into the fragment path 84 (FIG. 14A) while door 54' diverts items into return to hopper path 86 (FIG. 14B). Actually, the return to hopper path 86 is a return path to the pickup chamber 90 in this embodiment. The reject path 84 may have a gate (not shown) on the end to enable item fragments to be collected and held within the reject path 84. The functions of the paths 16, 84 and 86 are interchangeable. For example, the path 84 could be used for "good" items being dispensed while the path 16 could be used for rejects. Thus, references to paths, first and second paths, and the like should not be construed as being limited to a particular use for a path.

Figure 15A:
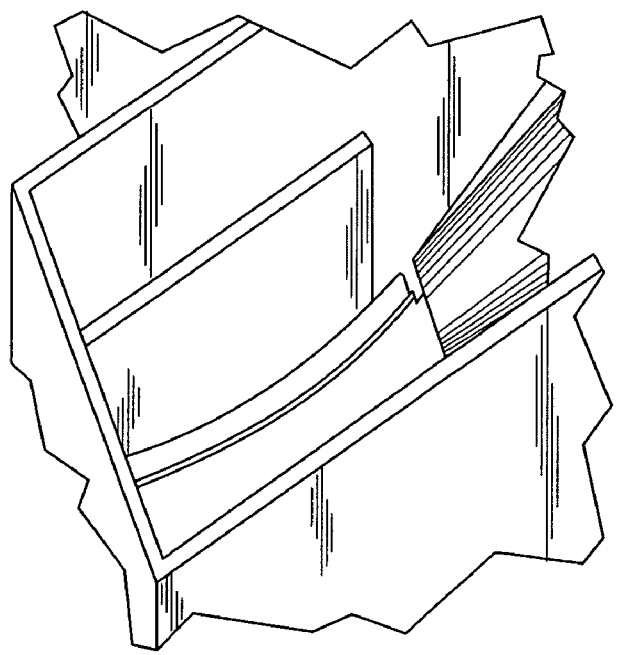
Figure 15B:
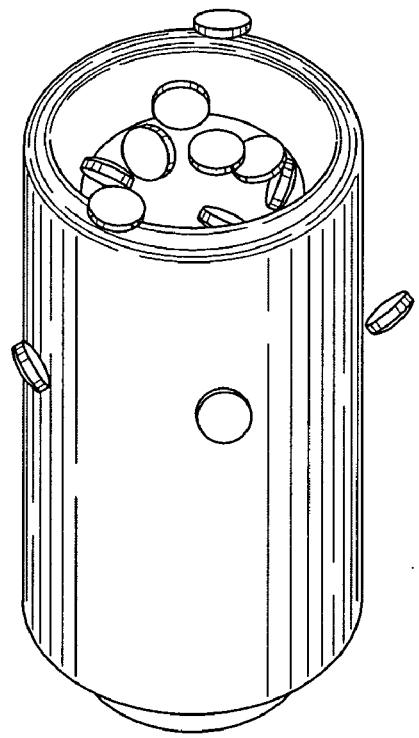

The hopper 12 may be comprised of a "feeding mechanism" that subjects only a certain amount of items to the singulating disc 20 at a time. Such a feeding mechanism could be implemented via a controlled gate as shown in FIG. 15A. Another feeding mechanism entails making all or a portion of the bottom surface of the hopper 12 a push-up feeder, see FIG. 15B, so that as the bottom advances at a specified rate, items spill over the top and fall to the singulating disc interface at a controlled rate.

Figure 15C:
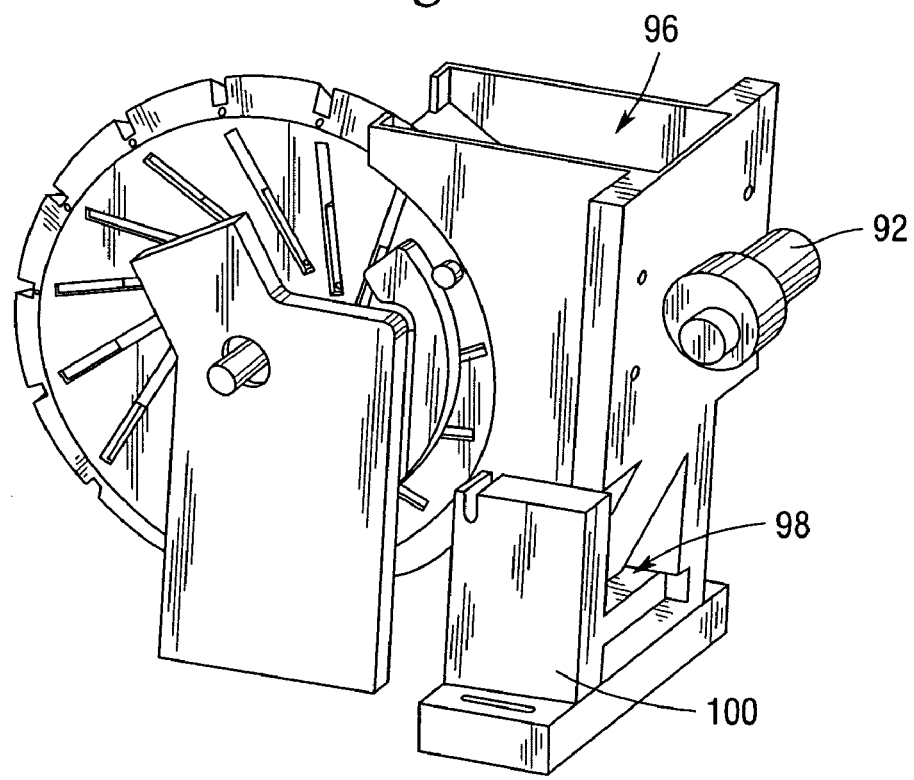
FIG. 15C illustrates a vibrating hopper embodiment.

Another mechanism for aiding the flow of pills down the hopper into the vicinity of the pickup sector 32 is vibration. Vibration helps to dislodge the pills and decreases friction so that the pills may move more freely. By utilizing a mechanism to vibrate some or all of the hopper, the pills will flow to the hopper-disc interface and eventually be picked up by the paddles (See FIG. 17A), or the nozzles, openings, etc. with which the disc is fitted. The vibration may be implemented in a number of ways, one of which is illustrated in FIG. 15C. In FIG. 15C, vibration is accomplished using an eccentric mass 92 mounted to a motor 94 which in turn is mounted to the hopper 96. The motor 94 can be run at a number of different speeds to accomplish different frequencies of vibration. The motor is mounted about an axis parallel to the axis rotation of the disc. Mounting in that manner insures that the vibration is contained in the plane of the disc. Therefore, the vibration will not affect the alignment of the paddle pins (See FIG. 17A) with the hopper chamber. Also, the hopper 96 may be mounted on a rotating shaft to further constrain the motion in that plane. An adjustable rail 98 may be provided in the back of the hopper to adjust the amplitude of vibration. The adjustable rail 98 can be moved so as to tighten or loosen the amount of contact between the hopper 96 and the hopper stand 100.

According to another embodiment, of the present invention, the removable hopper 12 (See FIG. 13A) may be provided with a radio frequency identification (RFID) tag and the singulating device and counter 10 may be provided with an RFID tag reader. In that embodiment, when a removable hopper 12 is connected to the singulating device and counter 10, the RFID reader interrogates the RFID tag carried by the hopper 12 to verify that the proper hopper is connected for the item to be dispensed. If the RFID tag is a read/write type of tag, additional information could be stored such as the quantity of items left in the hopper, a desire par level for that item, expiration dates, shelf location where the hopper is to be stored, etc. Maintenance history or any other information associated with the hopper could be written to the RFID tag.

Figure 18:
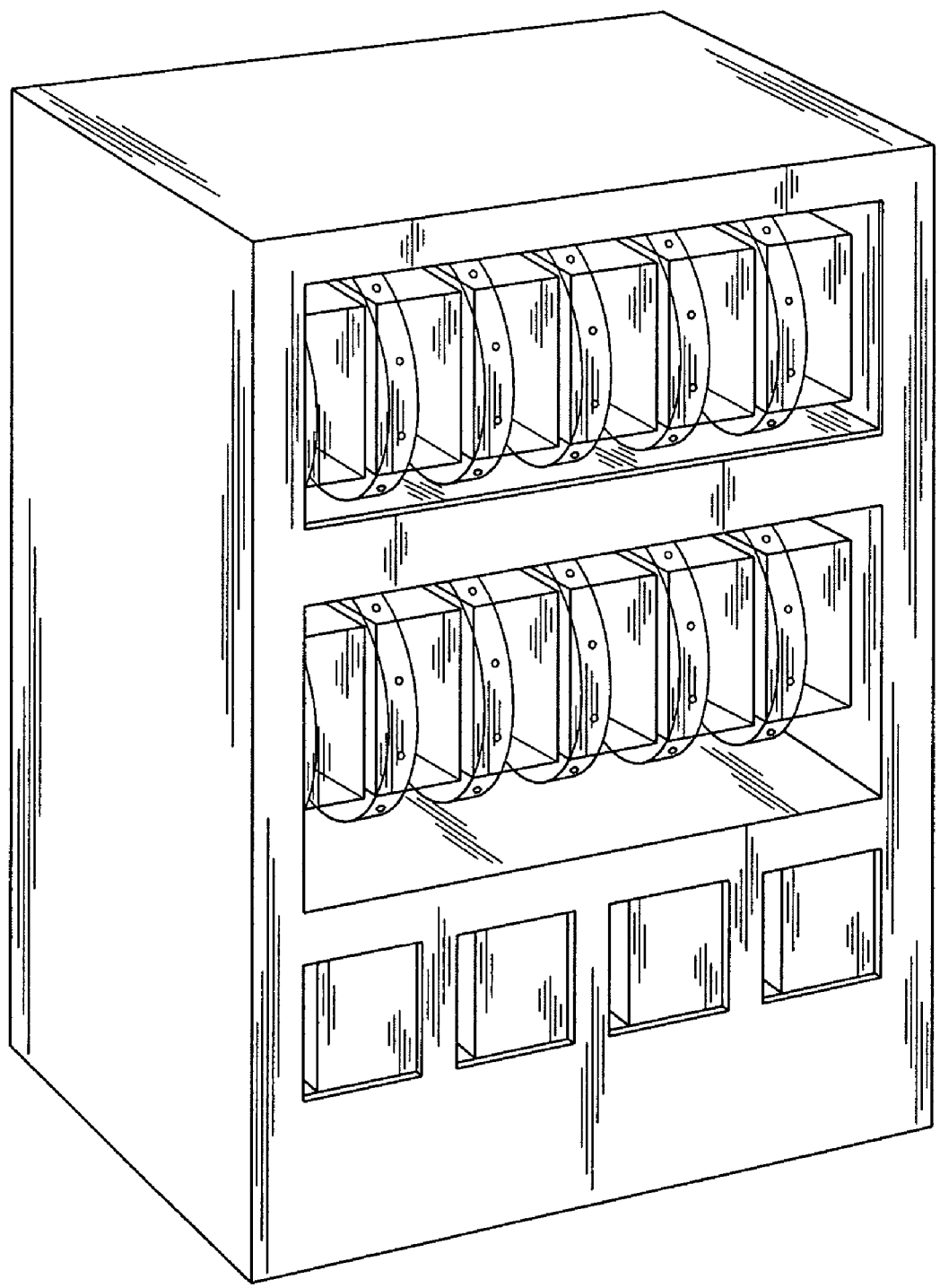
FIG. 18 illustrates a "vending machine" type of embodiment in which the present disclosure may be used.

The present disclosure may be used as a module type counter that can be utilized in different embodiments. As a stand-alone counter, detachable hoppers may be designed to interface with a single counter. In a cell embodiment, i.e. an embodiment comprised of an array or bank of hoppers, dedicated hoppers for each counter are arranged in an array. Different items are assigned to each cell. An advantage of the use of this disclosure in a cell embodiment is that no calibration is needed to switch items in a cell. Use of this device in a vending machine embodiment, see FIG. 18, involves multiple discs incorporated in series to count a multitude of item types utilizing a compact space. The discs could all be run using one vacuum source and one motor. In another embodiment, two or more discs could be incorporated into one counter to increase the speed at which the items can be singulated. That also reduces the weight of items resting on one another in the hopper by spreading out the items along multiple discs.

Figure 19:
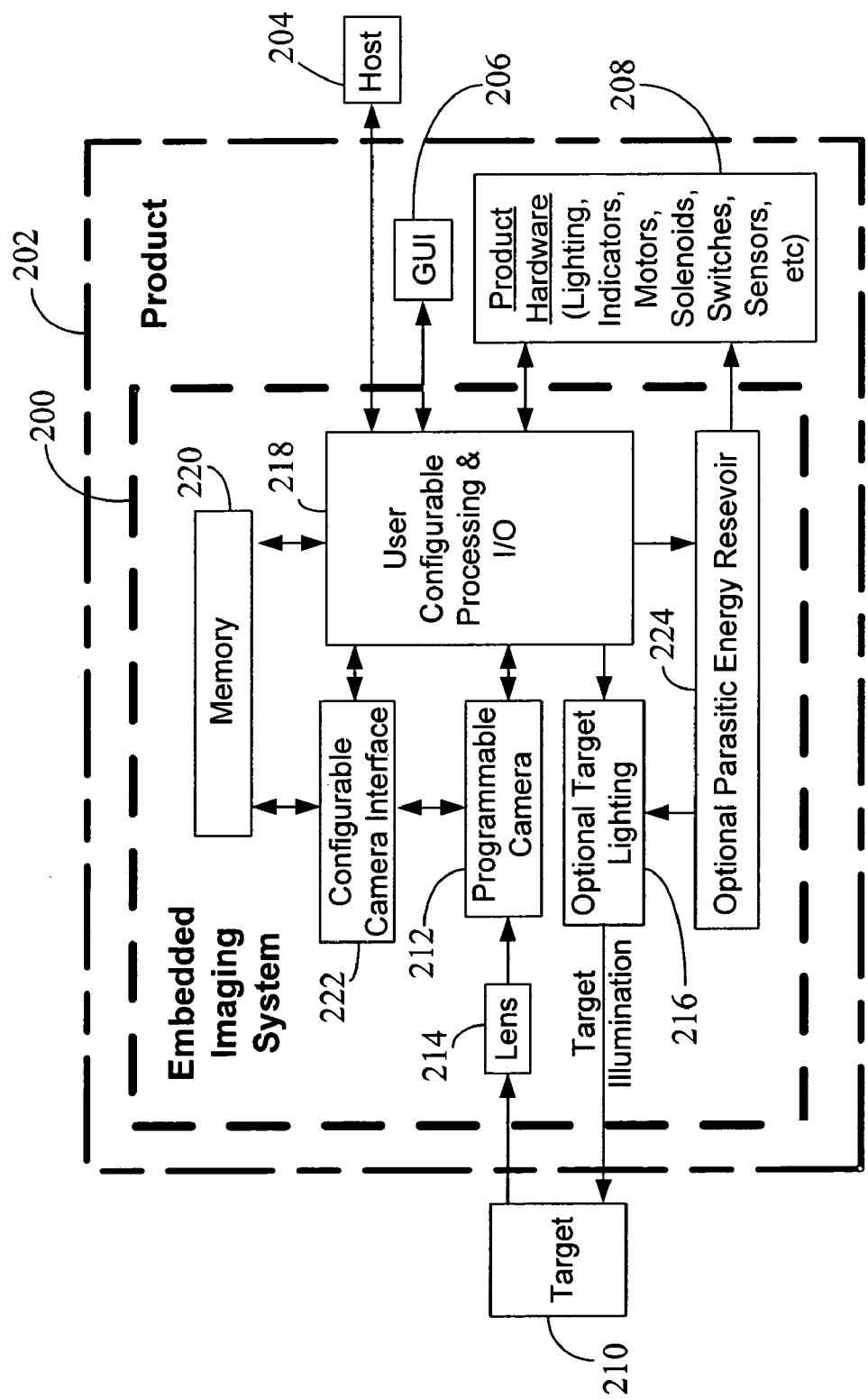
FIG. 19 shows a high level block diagram of an exemplary embodiment of an embedded imaging system according to the present disclosure.

FIG. 19 shows a high level block diagram of an exemplary embodiment of an embedded sensor or imaging system 200 according to the present disclosure which may be used with the singulating device and counter previously described. The imaging system 200 is shown embedded in a typical generic product or unit 202. In this embodiment, the system 200 is doing more than taking images and handling image processing as discussed in detail hereinbelow. The sensor system 200 is interfaced to both a high level host 204 (which can be a PC (Personal Computer) or a work station, either stand alone or in a networked configuration) and a GUI 206 on the unit 202, with each connection using a communications port. The system 200 is also shown connected to and/or controlling external hardware 208 (of the product 202), including motors, lighting and sensors. Other components illustrated in FIG. 19 are discussed hereinbelow at relevant places. It is noted here that the term "external" in the phrase "external hardware" used hereinabove refers to the hardware that may be physically external to the embedded imaging system 200, but integral to or part of the product 202.

To better understand the implementation of FIG. 19, it is useful to turn FIG. 19 into a more specific example. Assuming, for example, that the product 202 in FIG. 19 is a pill counting machine used in a pharmacy. The embedded imaging system 200 within the pill counting machine 202 would then utilize the external motor and sensors (the product hardware 208) of the pill counting machine 202 to position a stream of pills (or targets 210) in front of a programmable camera 212, i.e., in front of the lens 214 of the camera 212. The embedded imaging system 200 may then engage a lighting unit 216 (in preparation for taking a picture of the pill 210) and perform real time image processing (using a user configurable processing and I/O unit 218), when prompted by pill position sensors 208, located somewhere along the pill path (e.g., a conveyor belt or a chute) within the pill counting machine 202. Based on the processed image result, the embedded image system 200 may command the motor and solenoids 208 inside the pill counting machine 202 to drop the pill 210 in the "accept" or "reject" bin (not shown). In this example, the embedded imaging system 200 may also send a copy of the pill's image to the host 204 for archiving. Thus, the embedded sensor system 200 maintains a very flexible interface to the outside world, because most of the external I/O, communications and control requirements are application specific. This external interface will be discussed in much greater detail later hereinbelow.

Before proceeding further, it is preferable to discuss some examples where the sensor system 200 may be embedded inside a machine or product 202. The vision system 200 can be used, in conjunction with application specific vision based processes, to enable a machine 202 to: (1) Count or not count an object 210 or event. (2) Discriminate attributes about an object or event. Some examples of vision based discrimination include, but are not limited to, determining the object size, color, shape, orientation, spectra, position, identity and state of completeness or physical integrity (e.g., whether a pill is fragmented or not). (3) Obtain and/or store images (taken by the camera 212) which may be processed and/or unprocessed. (4) Obtain and/or transmit camera images which may be processed and/or unprocessed. (5) Assist with or perform object singulation (e.g., during pill counting) and/or object motion control. (6) Assist with or perform object orientation and/or positioning. (7) Perform a function or process such as, but not limited to, accepting or rejecting an object or event based on the results of the image processing. (8) Utilize multiple embedded imaging systems (e.g., when multiple embedded cameras and lighting units are needed) in a manner that enables an object or event to be viewed from multiple angles and/or positions and/or at different points in time. (9) Be used with a multiplicity of mirrors in a manner that enables an object or event to be viewed from multiple angles and/or positions and/or at different points in time. (10) Control additional external lighting sources. (11) Respond to instructions from an external computer (e.g., the host computer 204) or user interface (e.g., the GUI 206). (12) Perform a self or process calibration. (13) Use an optional parasitic energy reservoir 224 to insure that the embedded system 200 does not draw more power than the input can deliver without creating a fault condition. (14) Use the optional parasitic energy reservoir 224 to provide supplemental energy when the embedded vision system 200 requires more energy than the input power source can deliver. (15) Obtain and use continuous or semi-continuous images as feedback to control a real time packaging process.

Figure 20:
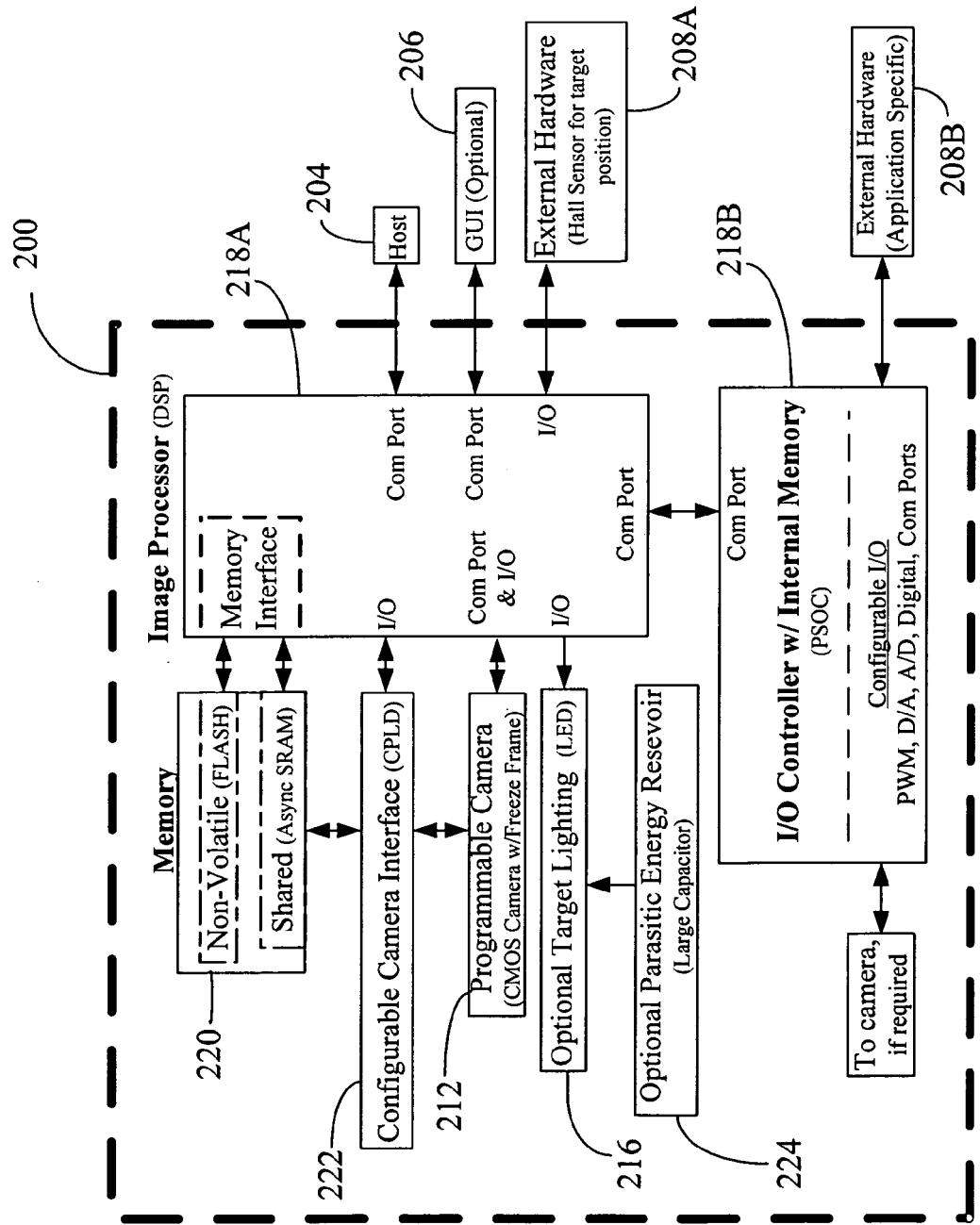
FIG. 20 shows the embedded imaging system of FIG. 19 subdivided into modular components.

FIG. 20 shows the embedded imaging system 200 of FIG. 19 subdivided into modular components, some of which are individually discussed below. The product hardware portion 208 in FIG. 19 is shown subdivided into two separate external hardware blocks 208A and 208B. The host 204 and GUI 206 are shown separate from the other external hardware 208A, 208B. The user configurable processing and I/O unit 218 is also shown functionally subdivided into two separate units—an image processor or DSP (digital signal processor) unit 218A, and an I/O controller 218B. The host and/or GUI can be connected to either the image processor 218A or the I/O controller 218B, depending upon the embodiment. For example, the application may require the image processor 218A to be almost fully occupied performing image processing, while at the same time a host 204 may require an instant response to every query. In that case, using a dedicated I/O controller 218B to supplement the image processor I/O could result in an embodiment that insures the host 204 will always receive an instant query response. In another example, the GUI 206 may have an unusual interface that is more efficiently handled by a dedicated I/O controller 218B than the image processor I/O, even though the image processor 218A could easily meet the timing constraints required by the GUI application. As discussed later hereinbelow, the term "I/O" takes on a broad meaning when used in the context of the present disclosure of the embedded imaging system 200. Those of ordinary skill in the art will recognize that FIG. 20 contains reference to both general functional blocks (such as "image processor" 218A, "memory" 220, etc.) as well as specific technologies (such as "DSP" or "flash"). The technology-specific information is provided for a better understanding of the present disclosure and is not meant to narrow the scope of the disclosure or the claims included hereinbelow. For example, rather than implementing the "image processor" functionality using a DSP, other technologies can be used as is known in the art. Some examples of alternative choices include microprocessor, FPGA, or ASIC (application specific integrated circuit). In the like manner, each of the other functional blocks in FIG. 20 can be implemented using other alternative technologies.

Camera 212

The vision system 200 is an embedded automation application that captures one or more images of a moving object or target 210 and reacts to it. To avoid image blurring and meet the embedded system's requirements, the camera 212 should preferably meet the following general requirements: (1) Be extremely small. (2) Initiate image capture via an external trigger signal (e.g., from the DSP 218A via a corn port) (not shown). (3) Be able to capture the moving image (e.g., the image of a moving pill) with sufficient quality to meet the image processing requirements. Both the moving image and the image processing requirements are application specific. (4) Have a sufficient frame rate to satisfy the application on hand (e.g., pill counting, pill inspection, etc.). (5) The camera should preferably have an electronic shutter so that an image can be captured and transmitted electronically.

Insuring that the camera 212 can capture a good quality image may be accomplished by correctly specifying camera parameters that are consistent with the application on hand. This is a straight forward, routine task that can be performed with the help of any camera supplier. A partial list of camera parameters that may need to be specified includes: (1) The level of acceptable image blurring, rastering or any other motion related distortion; (2) image resolution; (3) camera field of view; (4) color and/or gray scale parameters; (5) light sensitivity; (6) image correction factors; (7) lighting requirements; (8) frame rate; (9) image integration time; and (10) image output format and method.

Most camera types, including those found in web cams, digital cameras, and cell phones have attributes that are inconsistent with at least one of the above general requirements. For example: (1) Progressive or interlace scan cameras integrate images one line at a time, as opposed to simultaneously integrating the entire image. This type of camera currently cannot capture an undistorted stop action image of an object moving at automation speeds, unless the automation speed is uncharacteristically slow. For example, a typical pharmacy automation machine dispenses pills at approximately 8 pills/sec. In this situation, an automation camera has 135 microseconds or less to capture each pill image to avoid unacceptable image blurring. Progressing scan cameras are one hundred times too slow. (2) Cameras that send continuous streaming video usually lack the ability to initiate a new image capture via a user controlled trigger signal. Unless the camera has a very high frame rate relative to the object speed, these cameras cannot insure that they will always capture the moving object in the desired field of view. (3) Some cameras are too large because of the technology they employ. For example, many consumer digital cameras employ CCD (Charge Coupled Device) camera sensors which require specialized support ICs (Integrated Circuits) to provide numerous timing signals and voltages. These support ICs frequently add size and an overly complicated interface that makes such digital cameras too large for many deeply embedded applications. (4) The size of the camera lens also matters in an embedded application. If the camera employs lenses that are too big, then the camera is unusable. Cameras that employ an adjustable or full body lens generally are too large to be used in embedded applications.

The embodiment of FIG. 20 uses a new camera IC (for the camera unit 212) specifically designed for the automation market. The IC is a ½ inch CMOS active pixel image sensor, part number MT9V403C125STC, produced by Micron Technology, Inc. It is a sensor that can provide true stop action, high frame rate, high resolution images of moving objects. The camera freeze-frame electronic shutter enables the signal charges of all the frame pixels to be integrated at the same time. This type of camera, fitted with a miniature lens, is preferable for embedded applications contemplated by the present disclosure.

It is observed here that the image-taking according to the present disclosure is not limited to taking of images of a visual field (or visual images). On the contrary, the imaging system 200 may be devised for an application involving taking of electromagnetic (visual and non-visual) images of a camera's field of view. In that case, the camera 212 may be any one of the following: an infrared camera, an NIR (Near Infrared) camera, an SWIR (Short Wave Infrared) camera, an X-ray imaging camera, an ultrasonic camera, etc. Thus, the camera 212 may be a conventional visual-field camera (e.g., a web cam or a digital camera) or a non-visual field, electromagnetic image capture camera (e.g., an infrared camera). An NIR camera, for example, may be used in a robotic seam tracking application discussed later hereinbelow.

Configurable Camera Interface 222

The configurable camera interface module 222 may perform the following functions: (1) Generating any external timing signals or voltages the camera 212 requires. (2) Transferring images from the camera 212 to the memory module 220 (discussed later hereinbelow). In one embodiment, the configurable camera interface 222 performs these image transfers without external supervision or assistance. (3) Providing some method whereby the processor can know that a new image is in memory. This can be accomplished by notifying the processor directly, setting a status bit in the configurable camera interface hardware, or loading the image status in a memory location. (4) Being reconfigurable to accommodate different camera sensors with no or minimal impact on the other system modules.

Figure 21:
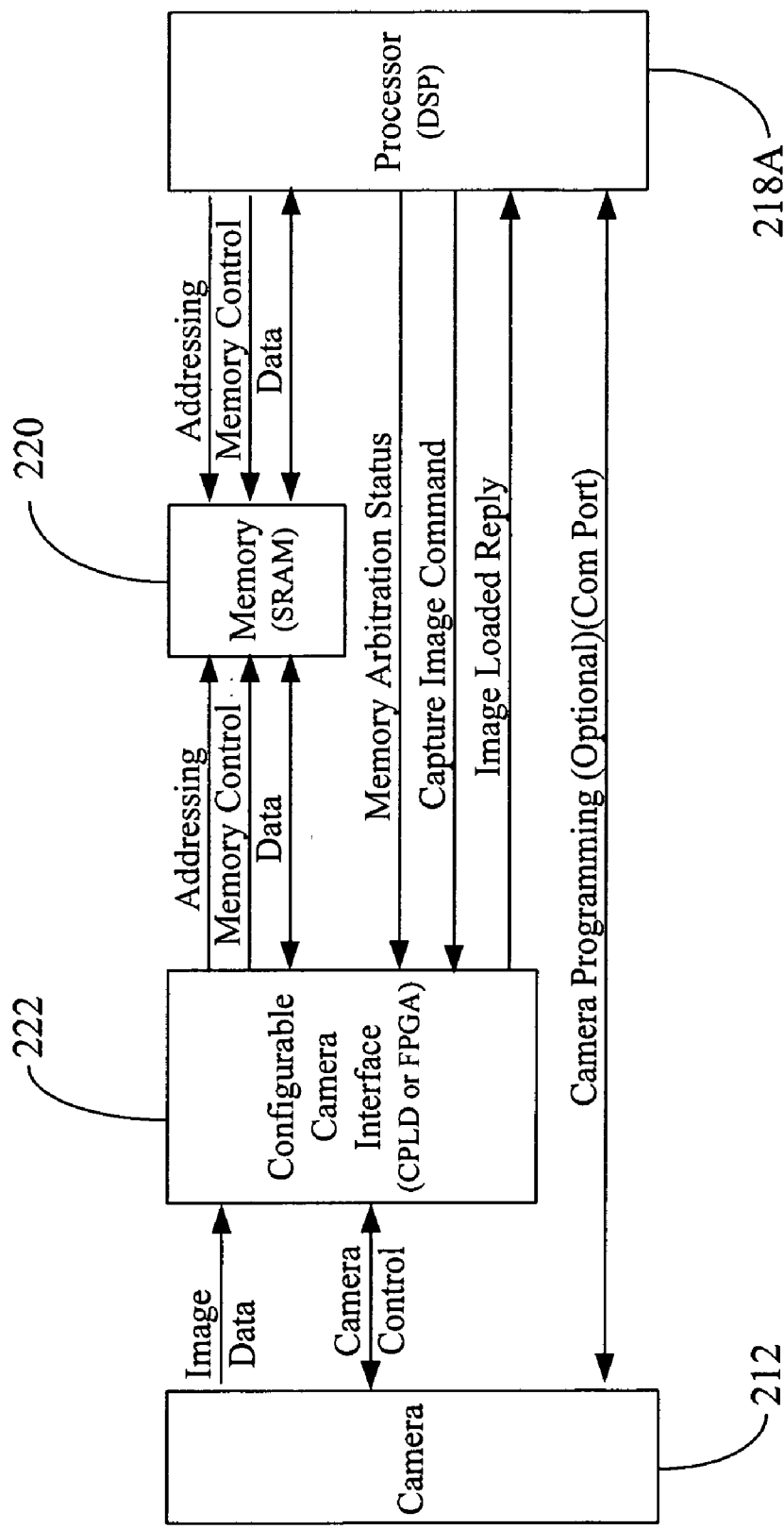
FIG. 21 shows how both the camera and the configurable camera interface are connected within the imaging system in the embodiment of FIG. 20.

FIG. 21 shows how both the camera 212 and the configurable camera interface 222 are connected within the imaging system 200 in the embodiment of FIG. 20. In the embodiment of FIG. 21, the processor 218A has minimal involvement with the camera. The processor 218A may perform only two camera functions. The first is to load any required camera parameters (into the camera 212), and the second is to initiate an image capture command and then wait for the reply (from the camera interface 222) indicating the image is captured and loaded into memory. In one embodiment, the processor uses one of two methods to program the camera. The first method is to communicate directly with the camera 212 using a dedicated corn port as shown in FIG. 21. The other method is to load the camera parameters into the SRAM (Static Random Access Memory) portion of the memory 220 so that the parameters are available for the configurable camera interface 222 to download and use them to program the camera 212.

Initiating an image capture from the processor 218A may require performance of two steps. First, the processor 218A may relinquish memory control to the configurable camera interface 222. This can be accomplished using the Memory Arbitration Status line shown in FIG. 21. This enables the configurable camera interface 222 to then "arm" the camera 212 by preparing for a "Capture Image" command. For example, the flexible camera interface 222 may need to program the camera 212 at this time with parameters that the processor 218A previously loaded into memory 220. In the second step, the processor 218A may issue the "Capture Image" command to the configurable camera interface 222, which results in a command to the camera 212 to capture an image. Once an image is captured, the flexible camera interface 222 loads the image into the memory 220 and sends an "Image Loaded" reply to the processor 218A so that the processor can take back control of the memory 220 using the Memory Arbitration Status signal.

In the embodiment of FIG. 21, the process of capturing the image and loading it into the memory 220 may be accomplished with minimal involvement from the processor 218A. The architecture of FIG. 21 thus allows the camera 212 to be easily changed with minimal impact to the processor 218A, the processor software and the configurable camera interface hardware 222. In one embodiment, the configurable camera interface 222 is a software configurable CPLD (Complex Programmable Logic Device) or FPGA (Field Programmable Gate Array). Although this architecture is best suited to interfacing with generic CMOS (Complimentary Metal Oxide Semiconductor) imaging sensors, almost any CCD camera, with its supporting timing and voltage control support ICs, could also be used, as long as the CCD sensor meets the cost and size constraints of the desired system 200.

It is observed that there may be two potential advantages to using a CPLD or FPGA in the configurable camera interface 222. First, the CPLD or FPGA can be easily configured to handle the handshaking required to operate any camera and then export the data to memory 220, without processor assistance. Second, a CPLD or FPGA can also be easily configured to convert any camera output into the fixed image format expected by the processor 218A. For example, one embodiment of the invention used a camera that produced image data that was finer than required and had a format that was unusable by the processor 218A in its raw form. As a result, the CPLD was software configured to drop unnecessary lower resolution image bits and then repackage and store the image data in the data format required by the processor 218A.

Memory 220

The discrete memory 220 may be connected to both the processor 218A and the camera flexible interface 222 as shown in FIG. 21. The memory 220 may store images captured by the camera 212 and any data the processor 218A needs to store there. In another embodiment, the memory 220 may also be used to store the processor and/or configurable camera interface program (if required). However, the present disclosure does not require these programs to be stored in the discrete memory 220 (as opposed to the processor's or interface's on board memories (not shown)), but allowing this possibility enables a wider selection of processor and configurable camera interface devices.

The memory size, speed and type may be determined based on the choice of processor, configurable camera interface and the application on hand. In one embodiment, the DSP 218A has no provision for on board program storage. However, it does have large blocks of on board high speed RAM (Random Access Memory). The selected processor 218A may be designed to address the external memory 220 in 2M×16 blocks. That is, the external memory 220 may store 2M (Mega) of data words (of 16 bits each). Because the selected processor 218A may be set up to access external memory in 2M×16 blocks, the embodiment in FIG. 20 may contain 2M×16 of discrete asynchronous SRAM (Static Random Access Memory) for image storage and 2M×16 of discrete non-volatile flash memory for processor program storage. The 2M×16 flash memory may be large enough to store any processor program and the 2M×16 SRAM may be large enough to simultaneously store a dozen uncompressed VGA (Video Graphics Array) camera images. The large memory sizes may be beneficial in a research and development platform used to evaluate a large number of image processing algorithms for embedded automation applications. However, in commercial embodiments, the memory size may be smaller.

Although the processor program may be stored in flash memory, the processor 218A may copy sections of the program into the fast internal (or on-board) processor RAM or external SRAM during initialization to meet the fast image processing times. The speed of the SRAM in the memory module 220 may be a function of the application requirements. Furthermore, although in one embodiment little SRAM is required to store an uncompressed camera image, other embodiments could also incorporate image compression in the configurable camera interface 222 to further reduce the amount of SRAM used to store the camera images output by the camera 212. Several alternate viable memory technologies may also be selected based on cost and compatibility considerations. For example, the synchronous burst SRAM may be found compatible or incompatible depending on the selected processor. Similarly, SDRAM (Synchronous Dynamic Random Access Memory) and synchronous SRAM may or may not complicate the configurable camera interface 222.

Image Processor 218A

The image processor 218A may perform two functions. First, it may process camera images. Second, it may also perform image related post processing tasks. It is noted that the disclosure provided herein should not be construed to be limited to the specific type of image processing or post processing task that is discussed, because the embedded imaging system 200 according to the present disclosure can be used in a wide variety of embedded vision applications (some examples of which are discussed later hereinbelow), all of them cannot be described in detail herein for the sake of brevity. Further, the method the image processor 218A may use to accomplish the image processing and the post processing tasks may be a function of the hardware that is selected to implement the embedded imaging system 200. FIGS. 4-6 show three different embodiments where each embodiment has a different utility over the others.

Figure 22:
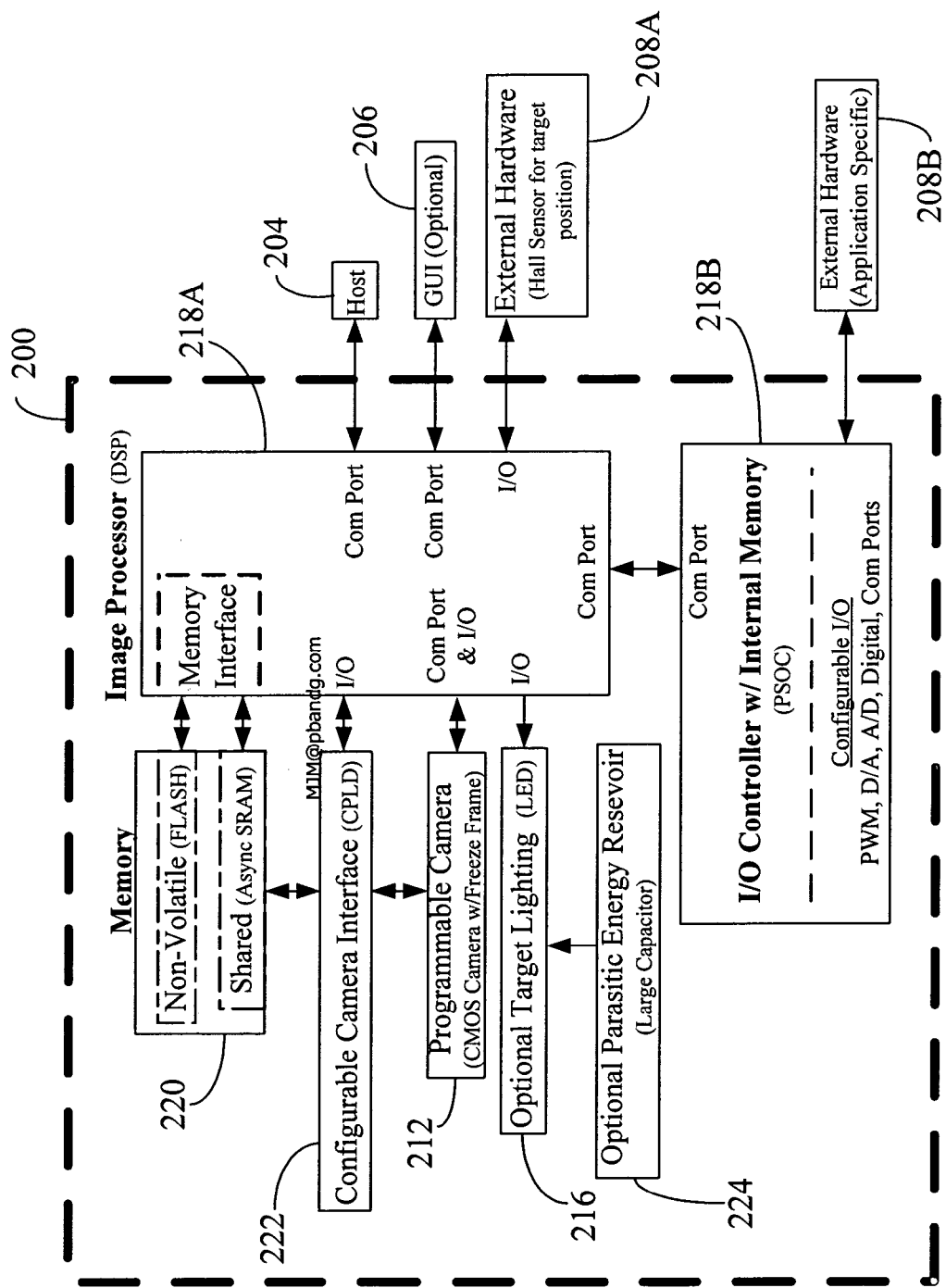
FIG. 22 illustrates an embodiment that utilizes the image processor in FIG. 20 to handle image related I/O and image processing.

FIG. 22 illustrates an embodiment that utilizes the image processor 218A in FIG. 20 to handle image related I/O and image processing. It is observed here that the embodiment illustrated in FIG. 22 is substantially similar in architecture to that shown in FIG. 20, where a separate I/O controller 218B is used to process non-image related I/O commands and tasks generated by the image processor 218A. In the embodiments of FIGS. 2 and 4, the image processor 218A is connected directly to the host 204 and/or a GUI 206 to enable direct host or GUI access/control of the image processing functions. After the image processing is complete, the image processor 218A may communicate a set of post processing commands to the I/O controller 218B, which the I/O controller may then execute. The embodiment in FIG. 22 has enough image processing power and I/O controller flexibility to handle a wide array of embedded vision applications by changing only the software and the external devices connected to the embedded imaging system 200.

The embodiment shown in FIG. 22 was constructed and tested to inspect pharmaceutical pills for fragmentation. The amount of fragmentation was determined by counting the number of image pixels that fell within a pre-determined color or gray scale range and comparing the number to an acceptable minimum. If the count was too low, it meant that the pill had unacceptably large amount of fragmentation. If the pill fell within expected parameters, the image processor 218A post processing algorithm commanded I/O controller 218B to direct the pill to a "good pill" location. If the image processing determined the pills fell outside the expected criteria (including pill quality criteria), then the post processing algorithm commanded I/O controller to move the object to a "pill rejected" location. In either case, the post processing algorithm also sent the pill images to a host 204 for archival storage and kept a running tally of the number of accepted and rejected pills. The embodiment in FIG. 22 may also be used to inspect other pill parameters by changes or additions to the image processing software described above. For example, a multiplicity of software algorithms for determining pill shapes and identifying features already exist, and one of these algorithms may be coded into the image processing software. Alternatively, a new software algorithm may be devised to accomplish the same task.

Figure 23:
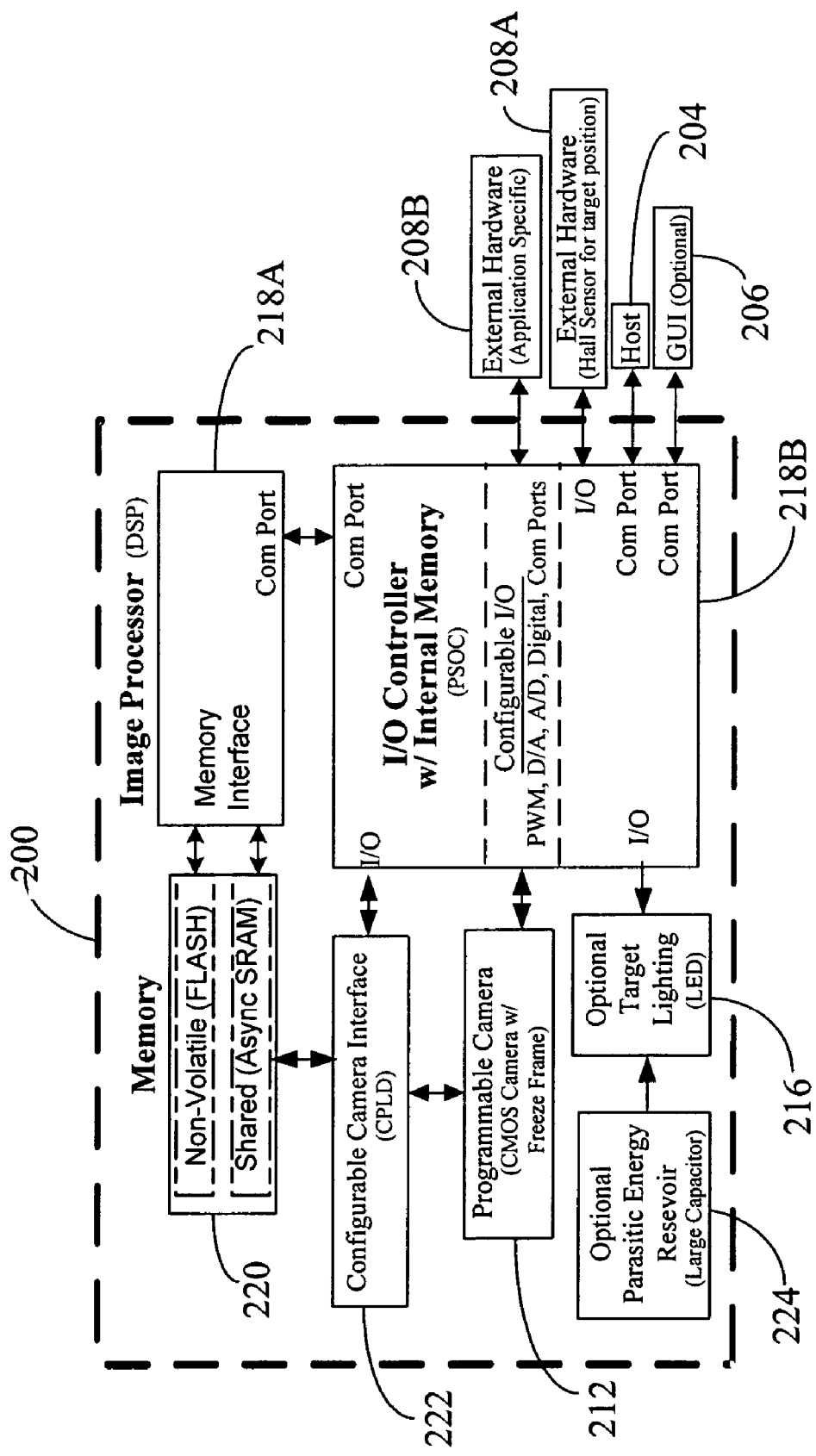
FIG. 23 shows an embodiment where the image processor of FIG. 20 has little or no I/O functionality.

FIG. 23 shows an embodiment where the image processor 218A of FIG. 20 has little or no I/O functionality. All I/O may be handled by the I/O controller 218B. An example of this embodiment would be the mating of a user selected DSP core with a microprocessor, microcontroller, PSOC (Programmable System On a Chip), ASIC, or FPGA. It is observed that the PSOC may be obtained from Cypress Semiconductor in Lynnwood, Wash. In this example, the DSP core has only enough I/O to interface to the FPGA, PSOC, ASIC, microprocessor, or microcontroller. All of the image processing would occur in the DSP (image processor 218A) and all of the image post processing decisions and commands would be generated in the DSP. However, in this embodiment, the DSP commands the I/O controller 218B, via the DSP to I/O controller connection, to perform any I/O tasks that are required because the DSP 218A lacks the on board I/O necessary to accomplish these tasks without assistance.

Figure 24:
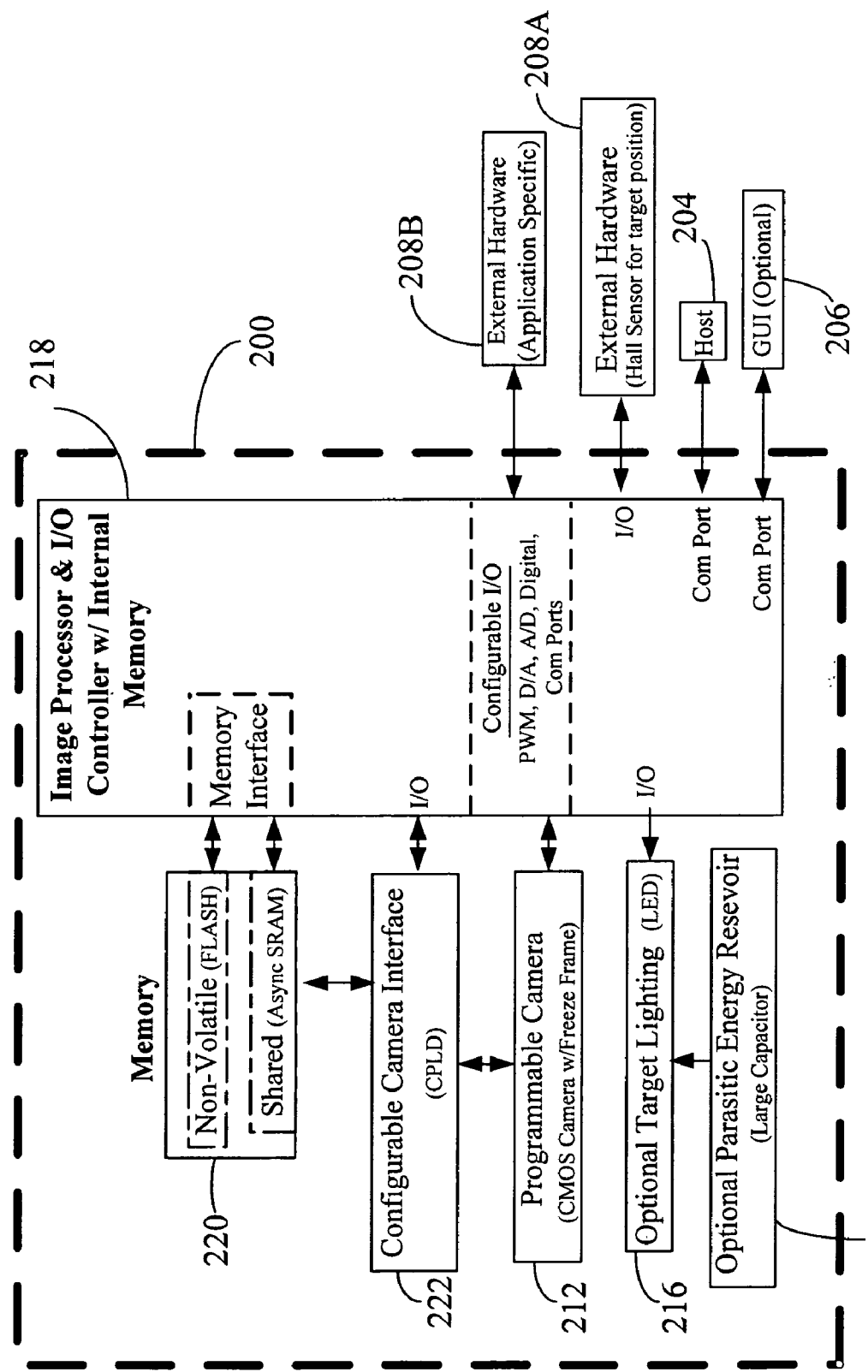
FIG. 24 shows an embodiment, similar to that shown in FIG. 19, where the image processor can handle all the image processing and post processing requirements without assistance from an external I/O controller.

FIG. 24 shows an embodiment, similar to that shown in FIG. 19, where the image processor 218 can handle all the image processing and post processing requirements without assistance from an external I/O controller. For the sake of clarity, the image processors in FIGS. 1 and 6 are designated by the same reference numeral "218." An example where the embodiment in FIG. 24 may be used is in the inspection of parts moving on a conveyor belt. If the image processor 218 determines that the part is bad, only a single digital I/O bit is required to activate a flipper and place the bad part into the trash bin. This is an example of an application where an image processor can be selected which can handle both the image processing and all of the I/O controller functions. It is noted that the architecture shown in FIG. 24 may be easily scaled up to cover even the most complex applications by simply altering the selection of the silicon device designated by the reference numeral "218." For example, a selection of the Altera Stratix 2 FPGA with Nios softcore IP technology (part number EP2S180) for silicon device "218" would place 96 separate DSPs and up to 1000 separate microprocessors all on a single piece of silicon, thereby affording a significant image processing and I/O control capability.

The selection of the image processor (218 or 218A depending on the configuration selected) is application specific. A partial list of some of the considerations includes: (1) the type of required image processing; (2) the required image processing speed; (3) memory interface criteria; (4) the number and type of available general purpose and communications I/O; (5) the amount and type of image processor's on board memory; (6) the availability and type of development tools; and (6) cost.

I/O Controller 218B

Both camera control and object motion control may be performed by I/O controller hardware which can reside in the image processor 218 (as in the embodiments of FIGS. 1 and 6), or in a separate I/O controller module (e.g., the I/O controller 218B in the embodiment of FIG. 23), or be split between the image processor 218A and a separate I/O controller module (e.g., the I/O controller 218B in the embodiments of FIGS. 2 and 4). In most applications, the selected image processor 218A may not have enough I/O capability and a separate I/O controller 2188B may be required to supplement the I/O capability of the image processor 218A. Another consideration for selecting a separate I/O controller block may be the desirability to maintain a true, real-time I/O control. If the image processor and the I/O controller functions are run out of the same processor core, then the processor time must be shared. In some applications, this can lead to an undesirable I/O control outcome where an I/O response did not occur fast enough.

The selection of the I/O controller 218B is usually application driven. For example, assume that the embedded imaging system 200 is part of a machine used to inspect parts moving on a conveyor belt and initiate a good/bad output bit that is used to push bad parts into a trash bin. In this example, the I/O controller 218B may be required to turn on and off the motor that is running the conveyor. The I/O controller 218B may even implement some operator safety interlock functions using simple combinational logic or a PAL (Programmable Array Logic) device. Conversely, assume that the application is to create an embedded imaging device for general purpose automation applications. In this example, the I/O controller 218B must be versatile enough and powerful enough to cover a wide variety of applications. The I/O controller 218B should probably include a large multiplicity of configurable I/O to supplement any I/O capability that the image processor 218A may possess to enable the embodiment to be used in a large variety of applications. The I/O controller should probably have a lot of digital I/O for sensor and interface control, multiple D/A and A/D for sensor interface, provisions for controlling motors using PWM pulses, and a multiplicity of different types and number of communications ports. In this example, a good choice for an I/O controller 218B may be a PSOC (Programmable System On a Chip) I/O controller, manufactured by Cypress Semiconductors of San Jose, Calif. This PSOC I/O controller has a multiplicity of the following types of I/O: configurable digital inputs and outputs, RS-232 communication ports, RS-485 communication ports, I2C communication ports, SPI (Serial Peripheral Interface) communication ports, configurable input and output D/A (Digital to Analog) converters, configurable input and output A/D (Analog to Digital) converters and configurable PWM (Pulse Width Modulated) outputs. All of the I/O functions are user selectable and programmable.

As mentioned hereinbefore, the embedded imaging system 200 may be used to inspect and disposition pharmaceutical pills. In that case, the I/O controller 218B may communicate with the image processor 218A using an SPI communications port. The I/O controller 218B may have an on-board microprocessor and internal memory that enable it to execute control programs initiated by commands from the image processor 218A. Some of these control programs may be executed pre-image processing, some may be executed concurrent with the image processing and some may be executed post-image processing. For example, one of the controller programs may output and monitor various camera reference voltages. A second control program may output PWM signals to control the motors that move the pills. A third control program may use digital outputs to command external hardware to move pills into dispense or reject bins, based on the image processing results.

Lighting Unit 216

It is observed that many embodiments of the imaging system 200 either incorporate lighting and/or have provisions to control external lighting. The lighting unit 216 is preferable because a fast camera shutter speed is required to prevent motion-related image distortion when the object (e.g., a pill) is moving fast and most cameras do not have sufficient light sensitivity to capture an image using a fast shutter speed unless additional object lighting is added. In one embodiment, the lighting is controlled by image processor I/O (as shown, for example, in FIGS. 1, 2, 4, and 6) or by a separate I/O controller module (as shown, for example, in FIG. 23). In one embodiment, the light intensity of the lighting unit 216 can also be adjusted and it may be insured that the light is on the full time that the image is being captured. The light source 216 may also be self-calibrated by the imaging system 200 upon system start-up. The easiest way to perform a lighting self calibration is to use a target. Upon power up, the camera may continuously image the target, adjusting the light intensity and/or the shutter speed up or down each time until the proper lighting level were achieved. The proper lighting level would correspond to the result that gives the best image of the target when compared with a library image (of the target). One way to accomplish this is to compare the lightness and darkness of specific points on the calibration-time target image with the same points taken from the library image (of the target). The target should preferably be small enough so that during normal system operation, the target would be completely covered by the object being imaged. Some of the factors affecting the required magnitude, duration and spectra of the lighting are the camera light sensitivity, the camera shutter speed, the distance of the camera to the object and the distance of the light to the target.

Parasitic Energy Reservoir 224

Some embodiments of the embedded imaging system 200 may include a parasitic energy reservoir 224. The parasitic energy reservoir 224 may insure that the vision system 200 does not draw more power than the input can deliver without creating a fault condition. Second, the reservoir 224 may provide supplemental energy when the vision system 200 requires more energy than the input power source can deliver. The method of constructing the parasitic energy reservoir 224 may be application specific. For example, in a pill counting and sorting embodiment, the optional parasitic energy reservoir 224 may be incorporated as part of the imaging system 200 because the peak power requirements of the embodiment may exceed what the input power source can deliver. For example, when a USB (Universal Serial Bus) port, which delivers a maximum of 2.5 W, is used as the input power source, the 2.5 watts of power is sufficient for most functions that the imaging system 200 performs. However, to capture images, the imaging system 200 temporarily turns on a high intensity light (using, for example, the optional lighting unit 216). In one embodiment, when the light is on, the total required power exceeds 6.2 watts. In that case, 6.2 watt power requirement may be met by using the optional parasitic energy reservoir 224 to provide supplemental power for the short time that the light is on. When the light is off, low levels of parasitic energy are drawn from the low output power source to trickle charge the very large energy reservoir 224. Because the time that the light is on may be very short (e.g., 140 microseconds or so), and because the total duty cycle of the light pulse (from the lighting unit 216) may also be very small (e.g., around 0.22%), it is possible to completely recharge the parasitic energy reservoir 224 in the time between each use of the light.

Figure 25A:
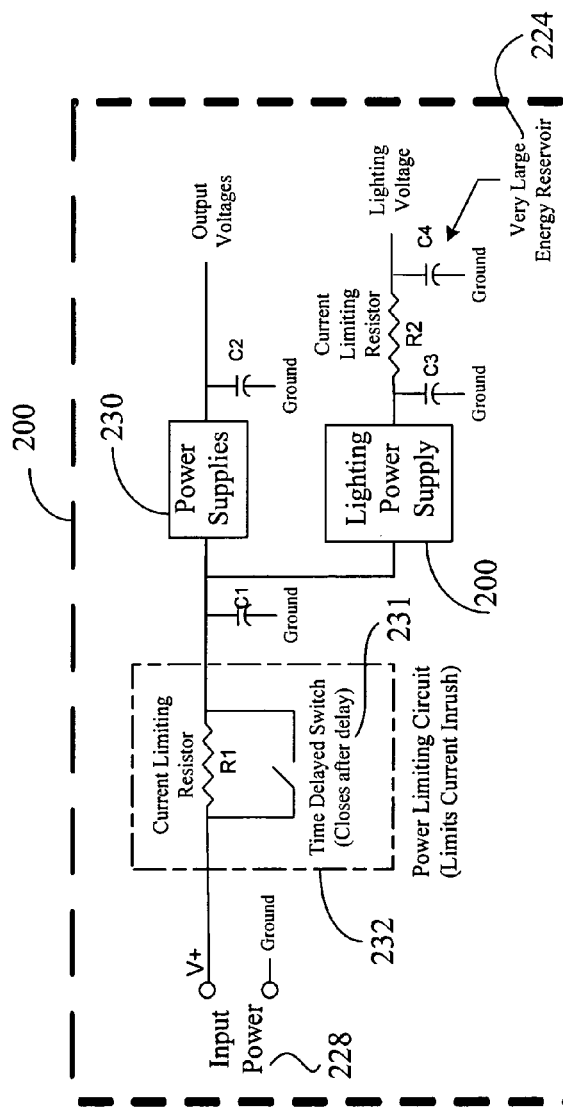
FIG. 25A illustrates how the optional parasitic energy reservoir may be implemented in one embodiment of the embedded imaging system in FIG. 19.

The imaging system 200 may also draw more power than the USB can supply when it is first connected to the power source. This may be because the system 200 is trying to charge internal circuits as fast as possible. This problem may be solved by employing circuits that slow the charge time of the electronics when power is first applied. FIG. 25A illustrates how the optional parasitic energy reservoir 224 may be implemented in one embodiment of the embedded imaging system 200 in FIG. 19. The only electronics shown in FIG. 25A is power related. Circuits showing the camera 212, image processor 218, configurable camera interface 222, memory 220 and optional lighting unit 216 have all been removed. Only circuits relating to the flow of power are shown.

In the embodiment of FIG. 25A, a USB port is utilized as the input power source 228 to deliver a maximum of 500 mA. However, the power supplies 230 used in the embodiment of FIG. 25A initially required more than 500 mA, when the input power is connected, because the power supplies have input capacitors (represented by "C1" in FIG. 25A) that needed to be charged. Without some type of power limiting circuit (e.g., the circuit 232 in FIG. 25A discussed below) between the input power and the power supply inputs, the embodiment would draw much more than the 500 mA the USB can deliver. This would cause the input power source (the USB) to declare a fault condition and stop delivering power. Therefore, three power limiting circuits are employed in the embodiment of FIG. 25A.

Figure 25B:
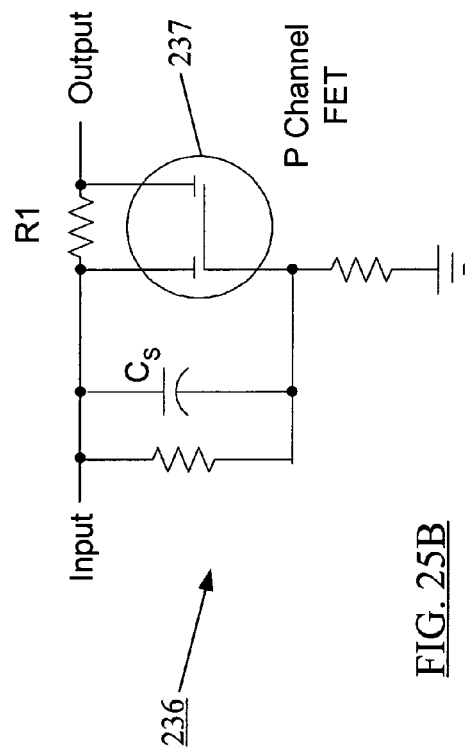
FIG. 25B shows an exemplary P-channel FET switch that may be used in the circuit configuration of FIG. 25A.

The first power limiting circuit 232 may be connected between the input power source (USB) 228 and the imaging system's 200 power conversion and distribution circuits (the power supplies 230). This circuit 232 uses a single resistor (R1) to limit the current the imaging system 200 can draw when the power source 228 is connected. Although the resistor R1 limits the input current, it also enables the power supply input capacitors (represented by C1) and other power related circuits to charge. After a period of time consistent with the charging requirements of C1 and the power supplies, a switch 231 (in the limiting circuit 232) closes, shorting out the current limiting resistor (R1) as shown in the configuration of FIG. 25A. After the switch 231 is closed, C1 and the power supplies 230 may continue to draw power, but they will do so at a rate that will preferably not exceed the maximum that can be delivered by the input power source 228. Shorting out the resistor R1 may be necessary to insure that both the full current and the full voltage are available as the input to the imaging system 200. FIG. 25B illustrates an exemplary switch configuration 236 for the switch 231 shown in FIG. 25A. A P-Channel FET (Field Effect Transistor) switch 236 in FIG. 25B may be used as the switch 231 in FIG. 25A to short out the resistor R1. The closing delay may be accomplished by placing a capacitor Cs (shown in FIG. 25B) in the FET bias circuit in FIG. 25B. The input power source 228 may charge the timing capacitor Cs in the FET bias circuit, which would cause the FET 237 to turn on and short out the resistor R1 after a predetermined amount of time. In one embodiment of FIG. 25B, the P-channel FET 237 is the FET with part number IRWL6401, the capacitor Cs has a value of 4.7 mf, the resistor between the gate of the FET 237 and the ground is of 1 kΩ, the resistor in parallel with Cs is of 10 kΩ, and resistor R1=10Ω, ½ W.

A second type of power limiting circuit ("soft start") (not shown) typically exists inside each power supply 230 if supplies with this feature are selected. However, the power supply soft start circuits may not affect the amount of power going to the supply input capacitors (C1). This is why the power limiting circuit 232 that uses R1 may be required. However, the power supply soft start circuits (not shown) can control the amount of power sent to everything on the power supply outputs, including the capacitors represented by C2-C4. The limiting circuits (not shown) in the power supplies 230 may be programmed: (1) To insure that the supplies 230 did not start producing power until after the power supply input capacitors (C1) were fully charged. The input capacitors need to be charged to insure the supplies work properly. (2) To insure that everything on the outputs of the power supplies 230 would charge at a rate that did not exceed the input power source (e.g., a USB source) capability.

The third power limiting circuit is represented in FIG. 25A as a resistor (R2) placed between the large energy reservoir 224 (represented by C4) and the lighting power supply 234 that feeds the reservoir 224. This power limiting circuit (R2) may insure that any load placed on the energy reservoir 224 will not result in an excess current draw upon the input power source 228. Furthermore, R2 may also serve the function of constantly replenishing the energy reservoir 224 when parasitic energy is available. However, it is preferable to insure that R2 is small enough so that the energy reservoir 224 can be recharged fast enough to meet the required duty cycle of the lighting unit 216 (as discussed hereinbefore), while at the same time insuring that R2 is not so small that the result is an unacceptably high current demand on the input power source 228.

The reservoir 224 can be any energy storage device (such as a battery or a capacitor (e.g., the capacitor C4 in FIG. 25A)) that can provide supplemental energy when the embodiment requires more energy than the input power source can deliver. A special purpose capacitor (e.g., the capacitor C4) that has a very high farad rating and a very low series resistance may be used as the energy reservoir 224. These properties may be desirable so that the device can deliver very large current pulses in a very short amount of time. Most large capacitors and batteries produced today have an internal resistance that is too large to deliver the required current in embedded vision applications where the energy discharge cycles are in the 100 microsecond range. Therefore, care must be taken when selecting the size of the energy storage device to insure that it is large enough so that the reservoir voltage does not drop to an unacceptable level, while it is delivering power, due to charge depletion.

It is seen from the foregoing discussion that the embedded vision system 200 in FIG. 19 is more than just an image sensor or digital camera; it is a real time, embedded vision system that meets the following three criteria: 1) All of the vision capture, vision processing, I/O controller and I/O interface hardware in the vision system can fit inside a package that is small enough to reside inside most machines that would employ such a device. 2) All of the image capture and processing as well as all the I/O processing and I/O control can be performed in real time. 3) The embedded vision system is able to run off the available power (e.g., a USB source).

Thus, as seen, the imaging system 200 according to the present disclosure may be embedded in a pill counting and sorting machine to process an image of the pill, use the image to make a decision about whether the pill should be dispensed or not and control all the other aspects of machine operation, which include host interface and all aspects of pill motion control. The integrated unit may also perform pill counting and discard fragmented or "bad" pills based on the real time processing of the pill's image. Additional applications of such embedded imaging system include, for example:

(1) Identifying fragmented pills, in real time, and quantifying the amount of fragmentation.
(2) Examining pills in real time and assigning a probability that each pill is the correct medication. This probability would be assigned by matching the pill color, size, shape and any identification markings with information (obtained from one or more "standard" or "ideal" pills) that exists in a data base.
(3) Providing a means of only counting and dispensing good pills because the I/O controller 218B may command bad pills to be disposed of. Thus, only pills of specific quality will be counted, rather than counting all pills regardless of pill quality.
(4) Snapping pill images and sending them to a remote location (e.g., the host computer 204). This enables a remote pharmacist to examine and verify if the pills are the correct medication.
(5) Complying with health laws. Some state laws require that an image of the medication appear on the label of the pill container. Current machines accomplish this by printing a library or "stock" image of the medication. This means the data base (of such stock images) must be updated every time a new drug is added to the system. If a generic is used, care must be taken to always use a generic from the same manufacturer because the same exact generic may look different if it is purchased from a different supplier. If the correct image is not in the image database, that pill cannot be dispensed. This can be a problem because new drugs or generics frequently arrive before their image database is made available. The imaging system 200 according to the present disclosure may therefore be used to locally create a pill image for the database, thereby speeding the introduction of new drugs or generics into the distribution system.
(6) Enabling the user to collect statistical data (about pills) that relates to quality control. The pharmacy can statistically build up an expected pill rejection rate for each medication and the imaging system 200 may be configured to alert a user when something is out of bounds. For example, an increased rejection rate might mean the dispensing machine needs to be cleaned. The user may also learn when a particular lot of pills has an uncharacteristically high amount of fragmentation.
(7) Controlling the pill dispenser. As discussed before, a dedicated I/O controller 218B may be used to perform all the functions of the dispensing system's existing hardware so as to carry out all of the machine control and host interface functions.
(8) Expanding pill dispenser capabilities with little or no cost impact. The embedded imaging system 200 may be a low cost solution that can do more than add vision capability to a pill dispenser. It can also replace the existing dispenser hardware that performs the machine control and host interface functions. As a result, the vision capability can be added at little or no extra cost.
(9) Functioning as a machine feedback control sensor in addition to functioning as a pill inspection device. One example of this application is to place the vision system 200 at the end of a robot arm (not shown) in a pill dispenser to provide arm position feedback and control. In this application, one low cost embedded vision system (such as the system 200 in FIG. 19) could replace multiple expensive optical encoders and the motion controller. The DSP 218A in the vision system 200 may be configured to perform the real time matrix calculations required to carry out simultaneous multi-axis robotic arm movements. In addition, there is no tasking conflict between performing the robotic arm calculations (which are required when the arm is moving) and the pill imaging calculations (which occur when the arm is at rest).

While the present disclosure has been described in connection with preferred embodiments thereof, those of ordinary skill in the art will recognize that many modifications and variations are possible. The present disclosure is intended to be limited only by the following claims and not by the foregoing description which is intended to set forth the presently preferred embodiments.

What is claimed is:

1. A singulating device, comprising:
   a housing;
   a removable hopper defining a pickup chamber, said hopper being connectable to said housing;
   an RFID tag carried by said hopper;
   an RFID tag reader carried by said housing;
   a rotatable singulating disc carried by said housing, said disc having a plurality of openings around the periphery thereto, a portion of said disc rotating through said pickup chamber;
   a source of rotary motion coupled to said singulating disc;
   a vacuum source coupled to said singulating disc;
   a counting device; and
   means responsive to said counting device for removing items from said singulating disc;
   wherein said singulating disc includes a hollow disc having a plurality of retractable paddles extendable from said periphery, each of said paddles having an actuating device extending through an opening in a face of said singulating disc, and a cam positioned to interface with each of said actuating devices during a portion of rotation of said singulating disc such that each of said devices moves along said opening in a first direction to cause its respective paddle to extend beyond said periphery, and to move along said opening in a second direction opposite to said first direction to cause said paddle to retract as said device rides along said cam.

2. The singulating device of claim 1 wherein said means responsive to said counting device includes a U-shaped mechanical diverter positioned adjacent to said periphery of said singulating disc, said diverter having a first position for directing items into a first path, a second position for directing items into a second path, and a third position which allows items to remain on said disc.

3. The singulating device of claim 1 wherein said RFID tag includes a tag into which information may be written.

4. The singulating device of claim 3 wherein said information includes at least one of a quantity of items in the hopper, a par level for that item, an expiration date for the items and a location where the hopper is stored.

5. A method of singulating items, comprising:
   rotating a singulating disc through a pickup chamber while pulling a vacuum at a plurality of openings located around the periphery of the disc;
   controlling the volume of air flowing through each of said plurality of openings;
   counting the items captured by the singulating disc;
   reading an RFID tag carried by a hopper in which the pickup chamber is formed; and
   dispensing the items captured by the singulating disc in response to said counting;
   wherein said dispensing includes removing the items captured by the singulating disc; and
   wherein said controlling includes maximizing the air flow through one of the plurality openings of the singulating disc when the opening is in the pickup chamber and minimizing the air flow through the opening during the removing of an item;
   wherein said controlling includes regulating the air flow so that the air flow through the opening is less than maximum but more than minimum during a portion of rotation of the disc from the pickup chamber until the removing of the item.

6. The method of claim 5 additionally comprising inspecting an item captured by the singulating disc to determine if the item may be dispensed.

7. The method of claim 5 additionally comprising controlling the extension and retraction of paddles from a periphery of the disc as the disc rotates.

8. The method of claim 7 additionally comprising ceasing the rotation of the disc and retracting all of said paddles.

9. The method of claim 8 including removing the hopper having the pickup chamber from a housing carrying the singulating disc.

10. A singulating device, comprising:
    a housing;
    a removable hopper defining a pickup chamber, said hopper being connectable to said housing;
    an RFID tag carried by said hopper;
    an RFID tag reader carried by said housing;
    a rotatable singulating disc carried by said housing, said disc having a plurality of openings around the periphery thereto, a portion of said disc rotating through said pickup chamber;
    a source of rotary motion coupled to said singulating disc;
    a vacuum source coupled to said singulating disc;
    a counting device; and
    means responsive to said counting device for removing items from said singulating disc;
    wherein said disc has a plurality of pistons, each piston positioned so as to control the flow of air flowing through one of said plurality of openings, and a cam positioned to interface with each of said pistons such that air flow is at a maximum for each opening while said opening is located in said pickup chamber and is at a minimum when said opening is positioned at said means for removing.

11. The singulating device of claim 10 wherein said means responsive to said counting device includes a U-shaped mechanical diverter positioned adjacent to said periphery of said singulating disc, said diverter having a first position for directing items into a first path, a second position for directing items into a second path, and a third position which allows items to remain on said disc.

12. The singulating device for claim 10 wherein said RFID tag includes a tag into which information may be written.

13. The singulating device of claim 12 wherein said information includes at least one of a quantity of items in the hopper, a par level for the items, an expiration date for the items and a location where the hopper is stored.

* * * * *